(12) United States Patent (10) Patent No.: US 9,394,569 B2
Arber (45) Date of Patent: Jul. 19, 2016

(54) METHODS AND KITS FOR EARLY DETECTION OF CANCER OR PREDISPOSITION THERETO

(75) Inventor: Nadir Arber, Tel-Aviv (IL)

(73) Assignee: The Medical Research, Infrastructure and Health Services Fund of the Tel Aviv Medical Center, Tel-Aviv (IL)

(*) Notice: Subject to any disclaimer, the term of this patent is extended or adjusted under 35 U.S.C. 154(b) by 432 days.

(21) Appl. No.: 12/223,315

(22) PCT Filed: Jan. 31, 2007

(86) PCT No.: PCT/IL2007/000122
§ 371 (c)(1),
(2), (4) Date: Jul. 29, 2008

(87) PCT Pub. No.: WO2007/088537
PCT Pub. Date: Aug. 9, 2007

(65) Prior Publication Data
US 2010/0062450 A1 Mar. 11, 2010

Related U.S. Application Data

(60) Provisional application No. 60/763,378, filed on Jan. 31, 2006.

(51) Int. Cl.
*G01N 33/53* (2006.01)
*C12Q 1/68* (2006.01)
*G01N 33/574* (2006.01)

(52) U.S. Cl.
CPC ........ *C12Q 1/6886* (2013.01); *G01N 33/57419* (2013.01); *G01N 33/57488* (2013.01); *C12Q 2600/118* (2013.01); *C12Q 2600/156* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 5,380,647 | A * | 1/1995 | Bahar | 435/7.23 |
| 5,741,650 | A * | 4/1998 | Lapidus et al. | 435/6.11 |
| 7,666,583 | B2 * | 2/2010 | Mor et al. | 435/4 |
| 2004/0005596 | A1 | 1/2004 | Li et al. | |
| 2004/0038220 | A1* | 2/2004 | Markowitz | 435/6 |
| 2004/0097448 | A1* | 5/2004 | Watt | 514/44 |
| 2005/0130193 | A1* | 6/2005 | Luxon et al. | 435/6 |
| 2009/0011407 | A1* | 1/2009 | Liu et al. | 435/6 |
| 2010/0062450 | A1 | 3/2010 | Arber | |

FOREIGN PATENT DOCUMENTS

| | | |
|---|---|---|
| CA | 2453198 | 7/2005 |
| WO | WO 2007/088537 | 8/2007 |

OTHER PUBLICATIONS

Andreola et al., J. Exp. Med., 2002, 195(10): 1303-1306.*
Kim et al., Annals Clin. Lab. Sci. 2003, 33(1): 32-38.*
Kristiansen et al. "Tumour Biological Aspects of CD24, A Mucin-Like Adhesion Molecule", Journal of Molecular Histology, 35: 255-262, 2004.
Sagiv et al. "CD24 Is a New Oncogene, Early at the Multistep Process of Colorectal Cancer Carcinogenesis", Gastroenterology, 131: 630-639, 2006.
Sagiv et al. "CD24 Plays an Important Role in the Carcinogenesis Process of the Pancreas", Biomedicine & Pharmacotherapy, 60(6): 280-284, 2006. Abstract.
Weichert et al "Cytoplasmic CD24 Expression in Colorectal Cancer Independently Correlates With Shortened Patient Survival", Clinical Cancer Research, 11(18): 6574-6581, 2005. p. 6575, r-h Col., Fig.3, Table 3, p. 6579, r-h Col.
Zhou et al. " CD24 Is a Genetic Modifier for Risk and Progression of Multiple Sclerosis", Proc. Natl. Acad. Sci. USA, 100(25): 15041-15046, 2003.
Communication Pursuant to Article 94(3) EPC Dated Apr. 8, 2009 From the European Patent Office Re.: Application No. 07706065.5.
Communication Relating to the Results of the Partial International Search Dated Jun. 4, 2007 From the International Searching Authority Re.: Application No. PCT/IL2007/000122.
International Preliminary Report on Patentability Dated Aug. 14, 2008 From the International Bureau of WIPO Re.: Application No. PCT/IL2007/000122.
International Search Report Dated Aug. 1, 2007 From the International Searching Authority Re.: Application No. PCT/IL2007/000122.
Written Opinion Dated Aug. 1, 2007 From the International Searching Authority Re.: Application No. PCT/IL2007/000122.
Response Dated Apr. 28, 2010 to Communication Pursuant to Article 94(3) EPC of Apr. 8, 2009 From the European Patent Office Re.: Application No. 07706065.5.
Office Action Dated Nov. 17, 2010 From the Israel Patent Office Re. Application No. 193097 and its Translation Into English.
Office Action Dated Aug. 3, 2011 From the Israel Patent Office Re. Application No. 193097 and its Translation Into English.
Translation of Notice of Reason for Rejection Dated Feb. 7, 2012 From the Japanese Patent Office Re. Application No. 2008-552953.
DePrimo et al. "Expression Profiling of Blood Samples From an SU5416 Phase III Metastatic Colorectal Cancer Clinical Trial: A Novel Strategy for Biomarker Identifiaction", BMC Cancer, 3(3): 1-12, Feb. 7, 2003.

(Continued)

*Primary Examiner* — Hong Sang

(57) ABSTRACT

Methods and kits for diagnosing cancer or a pre-malignant lesion by determining the presence and/or level of circulating CD24 of a subject are provided. Also provided are methods and kits for determining if a subject is predisposed to gastrointestinal cancer by the determining the presence or absence, in a homozygous or heterozygous form of cancer associated genotype(s) in the CD24 and/or APC nucleic acid sequences. Also provided are methods and kits for monitoring efficacy of cancer therapy by determining the presence and/or level of circulating CD24 of a subject.

5 Claims, 3 Drawing Sheets

(56) References Cited

OTHER PUBLICATIONS

He et al. "GPI-Specific Phospholipase D mRNA Expression in Tumor Cells of Different Malignancy", Clinical & Experimental Metastasis, 19(4): 291-299, 2002.
Yamamoto et al. "Cleavage of Carcinoembryonic Antigen Induces Metastatic Potential in Colorectal Carcinoma", Biochemical and Biophysical Research Communications, 333(1): 223-229, 2005.
Response Dated Dec. 4, 2011 to Office Action of Aug. 3, 2011 From the Israel Patent Office Re. Application No. 193097.
Office Action Dated May 17, 2012 From the Israel Patent Office Re. Application No. 193097 and its Translation Into English.
Translation of Notice of Reason for Rejection Dated Jun. 1, 2012 From the Japanese Patent Office Re. Application No. 2008-552953.
Response Dated Mar. 17, 2011 to Office Action of Nov. 17, 2010 From the Israel Patent Office Re. Application No. 193097.

* cited by examiner

METHODS AND KITS FOR EARLY DETECTION OF CANCER OR PREDISPOSITION THERETO

RELATED APPLICATIONS

This application is a National Phase Application of PCT Application No. PCT/IL2007/000122 having International Filing Date of Jan. 31, 2007, which claims the benefit of U.S. Provisional Patent Application No. 60/763,378, filed on Jan. 31, 2006. The contents of the above Applications are all incorporated herein by reference.

FIELD AND BACKGROUND OF THE INVENTION

The present invention relates to methods and kits for non-invasive, early detection of cancer and predisposition thereto using CD24, and more particularly, to methods and kits for diagnosing cancer or pre-malignant lesions by determining the expression level of soluble, shedded and/or blebbed CD24 in a biological sample.

Colorectal cancer (CRC) is a major health concern in the Western world as it is the third most common cancer in both men and women in the United States and Israel. This form of cancer develops through a stepwise process that involves a variety of genetic and epigenetic changes that are acquired over several years and eventually culminate in the transformation of normal epithelium into neoplasm. Although the disease has a long latency period, the currently available markers for disease detection are limited to invasive tests such as colon or gastric endoscopy, which often detect the disease while it has already been spread.

Mutations in oncogenes and tumor suppressor genes, abnormal gene expression and genetic defects in a variety of genes are intimately involved in CRC carcinogenesis. On the basis of the allelotypes of a series of colon tumors, Vogelstein and colleagues have showed that the molecular steps that occur after the activation of the APC-β-catenin—Tfc pathway involve a nonlinear accumulation of specific genetic changes that accompany the transition from normal colonic mucosa to metastatic carcinoma. These include mutations in the k-Ras oncogene, changes in methylation patterns, loss of DCC (Deleted in Colorectal Cancer gene) and SMADs [homologs of *drosophila* Mothers Against Decapentaplegic (MAD) protein, and the *C. elegans* protein SMA] and mutations in p53.

The currently available screening methods for cancers of the gastrointestinal tract (GI tract) such as colorectal cancer (CRC) include fecal occult blood testing (FOBT). However, although clinical trials have shown that screening with serial FOBT reduces CRC mortality (Mandel J, et al., 1993,), the sensitivity of FOBT is limited [60%; McMahon P M, et al., 2001]. Several markers have been recently suggested as non-invasive diagnostic tools. These include proteins [e.g., fecal calprotectin, lactoferrin, lysozyme, albumin, alpha-1-antitrypsin, carcinoembryonic antigen (CEA), decay-accelerating factor (DAF), minichrosomal maintenance protein (MCM2)] or mRNA (e.g., fecal COX-2) (Kanaoka S., et al., 2004) which can be detected in stool samples, and proteins such as nicotinamide N-methyltransferase (NNMT) (Roessler M, et al., 2005) or proteasome activator complex subunit 3 (PSME3) (Roessler M., et al., 2006), which can be detected in serum samples. However, due to their low sensitivity and specificity, these markers are not in clinical use.

CD24, also known as heat-stable antigen (HSA) in mice, is a heavily glycosilated phosphatidylinositol-anchored mucin-like cell-surface protein. Physiologically, the CD24 protein is expressed mainly on hematopoietic subpopulations of B lymphocytes, various epithelial cells, muscle and neural cells. It plays a crucial role in cell selection and maturation during hematopoiesis and is expressed during the embryonic period, on developing neural and pancreatic cells. In addition, CD24 is a potential ligand for P-selectin which functions as an adhesion molecule that enhances platelets aggregation.

The cellular function of CD24 is still unknown, but recent reports have strengthened its involvement in the initiation of intracellular signal transduction. Schabath et al. (Schabath H, et al., 2006) have associated the expression of CD24 with downregulation in the CXCR-4 chemokine receptor. In addition, CD24 is overexpressed in various malignant tissues including B-cell lymphomas, gliomas, small-cell and non-small cell lung, hepatocellular, renal cell, nasopharyngeal, bladder, uterine, epithelial ovarian, breast, prostate and pancreatic carcinomas (reviewed by Kristiansen et al., 2004). Moreover, its expression was found to correlate with increased growth rate, motility and survival in carcinoma cell lines derived from several organs (Baumann P, et al., 2005; Smith S C, et al., 2006) and with a more aggressive course of cancer. Thus, Weichert W., et al. (2005), found that increased expression of CD24 in the cytoplasm correlates with higher tumor stage, grade and presence of metastasis and concluded that overexpression of CD24 in the cytoplasm (as a result of over production or disturbances in distribution in the cell) is a marker for poorer prognosis. In addition, the role of CD24 in platelet aggregation may explain the involvement with cancer metastases and worse prognosis (Sammar, M., et al., 1994; Aigner, S., et al., 1997; Aigner, S., et al., 1998).

U.S. Pat. Appl. 20040005596 to Li J., et al., discloses methods of diagnosing cancer by determining the level of CD24 in situ in tissue samples suspected to be precancerous or cancerous, thus again necessitating invasional procedures for cancer detection.

There is thus a widely recognized need for, and it would be highly advantageous to have, a method of diagnosing cancer, especially at the pre-malignant stage, devoid of the above limitations.

SUMMARY OF THE INVENTION

According to one aspect of the present invention there is provided a method of diagnosing cancer or a pre-malignant lesion, the method comprising determining a presence and/or a level of a circulating CD24 of a subject in need thereof, wherein the presence and/or the level of the circulating CD24 above a predetermined threshold is indicative of the cancer or the pre-malignant lesion.

According to another aspect of the present invention there is provided a kit for diagnosing cancer or a pre-malignant lesion comprising a packaging material and at least one reagent for determining presence and/or level of circulating CD24 of a subject.

According to yet another aspect of the present invention there is provided a method of monitoring efficacy of cancer therapy, comprising determining a level of a circulating CD24 in a biological sample of the subject following the cancer therapy, wherein a decrease from a predetermined threshold in the level of the circulating CD24 following the cancer therapy is indicative of reduction of cancerous cells, thereby monitoring efficacy of the cancer therapy.

According to still another aspect of the present invention there is provided a method of determining if a subject is predisposed to gastrointestinal cancer, the method comprising determining a presence or absence, in a homozygous or heterozygous form, of at least one cancer-associated genotype in the CD24 nucleic acid sequence of the subject, thereby determining if the subject is predisposed to the gastrointestinal cancer.

According to an additional aspect of the present invention there is provided a kit for determining if a subject is predisposed to gastrointestinal cancer comprising a packaging material and at least one reagent for determining a presence or absence, in a homozygous or heterozygous form, of at least one cancer-associated genotype in the CD24 nucleic acid sequence of the subject.

According to yet an additional aspect of the present invention there is provided a kit for monitoring efficacy of cancer therapy, comprising packaging material and at least one reagent for determining a presence and/or a level of circulating CD24 of a subject.

According to further features in preferred embodiments of the invention described below, said pre-malignant region is an adenoma.

According to still further features in the described preferred embodiments determining is effected ex vivo.

According to still further features in the described preferred embodiments determining is effected in vivo.

According to still further features in the described preferred embodiments the CD24 comprises shedded CD24.

According to still further features in the described preferred embodiments the CD24 comprises blebbed CD24.

According to still further features in the described preferred embodiments the CD24 comprises soluble CD24.

According to still further features in the described preferred embodiments the pre-malignant lesion is associated with a solid tumor.

According to still further features in the described preferred embodiments the cancer is a solid tumor.

According to still further features in the described preferred embodiments the cancer is a gastrointestinal tract cancer.

According to still further features in the described preferred embodiments the pre-malignant lesion is associated with a gastrointestinal tract cancer.

According to still further features in the described preferred embodiments the gastrointestinal tract cancer is colorectal cancer.

According to still further features in the described preferred embodiments the pre-malignant lesion is associated with a cancer selected from the group consisting of lymphomas, gliomas, small-cell and non-small cell lung, hepatocellular, renal cell, nasopharyngeal, bladder, uterine, epithelial ovarian, breast, prostate and pancreatic carcinomas.

According to still further features in the described preferred embodiments the circulating CD24 is associated with a biological sample selected from the group consisting of a stool sample, a serum sample, a blood sample, a urine sample and a saliva sample.

According to still further features in the described preferred embodiments determining is effected at the protein level.

According to still further features in the described preferred embodiments the at least one reagent comprises a CD24 specific antibody.

According to still further features in the described preferred embodiments the at least one reagent comprises an oligonucleotide capable of specifically hybridizing to a CD24 nucleic acid sequence.

According to still further features in the described preferred embodiments the at least one cancer-associated genotype in the CD24 nucleic acid sequence is a thymidine nucleotide containing allele at position 280 of the polynucleotide set forth by SEQ ID NO:1.

According to still further features in the described preferred embodiments the method further comprising determining a presence or an absence, in a homozygous or heterozygous form, of at least one cancer-associated genotype in an APC nucleic acid sequence of the subject.

According to still further features in the described preferred embodiments the kit further comprising at least one reagent for determining a determining a presence or an absence, in a homozygous or heterozygous form, of at least one cancer-associated genotype in an APC nucleic acid sequence of the subject.

According to still further features in the described preferred embodiments the at least one cancer-associated genotype in the APC nucleic acid sequence is an adenosine nucleotide containing allele at position 3977 of the polynucleotide set forth by SEQ ID NO:7.

According to still further features in the described preferred embodiments the at least one cancer-associated genotype in the APC nucleic acid sequence is an cytosine nucleotide containing allele at position 4006 of the polynucleotide set forth by SEQ ID NO:7.

According to still further features in the described preferred embodiments the at least one cancer-associated genotype in the APC nucleic acid sequence is an adenosine nucleotide containing allele at position 3977 and a cytosine nucleotide containing allele at position 4006 of the polynucleotide set forth by SEQ ID NO:7

According to still further features in the described preferred embodiments the cancer therapy comprises radiation therapy.

According to still further features in the described preferred embodiments the cancer therapy comprises chemotherapy.

According to still further features in the described preferred embodiments the cancer therapy comprises antibody therapy.

According to still further features in the described preferred embodiments the kit further comprising instructions for use in monitoring efficacy of cancer therapy.

According to still further features in the described preferred embodiments the kit further comprising instructions for use in monitoring efficacy of cancer therapy.

According to still further features in the described preferred embodiments the kit further comprising instructions for use in determining if a subject is predisposed to gastrointestinal cancer.

According to still further features in the described preferred embodiments the kit further comprising instructions for use in diagnosing cancer or a pre-malignant lesion in a subject.

The present invention successfully addresses the shortcomings of the presently known configurations by providing methods and kits for diagnosing a pre-malignant lesion in a biological sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the biotechnological arts.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 2a—lanes 1-9: Lane 1—HT29 cells (positive control); lanes 2-3—P-1; lanes 4-5—P-2; lanes 6-7—P-3; lanes 8-9—P-4; FIG. 2b—lanes 10-18: lane 10—HT29 cells; lanes 11-12—P-5; lanes 13-14—P-6; lanes 15-16—P-7; lanes 17-18—P-8; FIG. 2c—lanes 19-27: lane 19—HT29 cells; lanes 20-21—P-9; lanes 22-23—P-10; lanes 24-25—P-11; lanes 26-27—P-12. Lanes 2, 4, 6, 8, 11, 15, 17, 20, 22, 24 and 26—samples were taken before the surgical removal of the tumor, lanes 3, 5, 7, 9, 12, 13, 14, 16, 18, 21, 23, 25 and 27—samples were taken after the surgical removal of the tumor. Note the significant decrease in CD24 levels following the surgical removal of tumors in at least 9 of 11 of the patients (e.g., compare the intensity of the protein band in lane 3 to that of lane 2), demonstrating that the presence of CD24 in the stool originates at least in part from the tumor. In addition, note that while in stool samples taken before the surgical removal of polyps or tumors the CD24-protein species include proteins of various sizes such as from about 20 to about 60 kDa (e.g., lanes 4, 17, 20 and 24), in stool samples taken after the surgical removal of the polyps or tumors the CD24-protein species include proteins of high molecular weight such as from about 37 to about 50 kDa (e.g., lanes 11, 18, 21). Also note the significant decrease in CD24 levels in stool samples obtained following radiation therapy (lane 14) as compared to those obtained before radiation therapy (lane 13), demonstrating that the level of CD24 in the stool originated from the malignant cells of CRC, thus a decrease in the level following treatment may indicate treatment efficiency (e.g., elimination of cancer cells).

DESCRIPTION OF THE PREFERRED EMBODIMENTS

Figure 1:
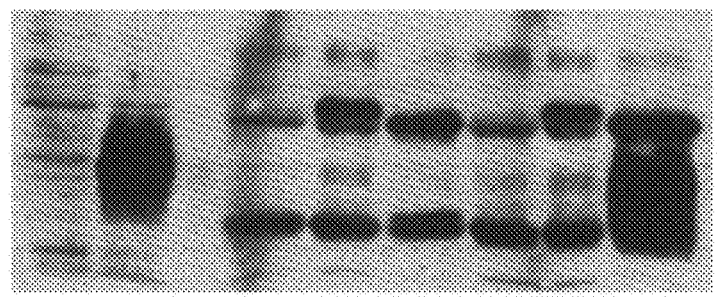
FIG. 1 is CD24—immunoprecipitation (IP) analysis of CRC cell lines. Extracts of the HCT116 (which do not express CD24) or HT29 (which express CD24) CRC cell lines were subjected to CD24-IP followed by Western blot analysis using the SWA11 CD24 antibody. Lane 1: Total lysate of HCT116 CRC cells (without IP); lane 2: total lysate of HT29 CRC cells (without IP); lanes 3-8—elution products of HCT116 cells (lanes 3-5) or HT29 cells (lanes 6-8) using anti-mouse conjugated Sepharose beads (Sigma): in the absence of IP antibody (first binder) (lanes 3 and 6), or following IP using the ML5 Ab (lanes 4 and 7) or the SWA11 Ab (lanes 5 and 8). Note the efficient IP using the SWA11 Ab to CD24 (lane 8), demonstrating that SWA11 is a suitable IP antibody, yielding low background.

The present invention relates to methods of early and non-invasive diagnosis of cancer or pre-malignant lesions using circulating CD24. In addition, the present invention is of high association of genotypes in the CD24 and APC genes with gastrointestinal cancer which can be used for detection predisposition thereto.

The principles and operation of the methods and kits of diagnosing pre-malignant lesions according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Cancers of the gastrointestinal (GI) tract, including colorectal cancer (CRC), develop over several years through a stepwise process in which genetic and epigenetic changes are acquired and eventually culminate in the transformation of normal epithelium into neoplasm. For example, CRC carcinogenesis involves mutations in oncogenes (e.g., k-Ras) and tumor suppressor genes (e.g., p53), changes in methylation patterns and loss of DCC and SMADs. However, in spite of the current genetic knowledge and the currently available endoscopy procedures (e.g., colonoscopy), at the time of diagnosis most of GI tract—related cancers have already spread and are more difficult to treat.

The currently available screening methods for cancers of the gastrointestinal tract (GI tract) such as colorectal cancer (CRC) include fecal occult blood testing (FOBT). However, although clinical trials have shown that screening with serial FOBT reduces CRC mortality, the sensitivity of FOBT is limited [60%; McMahon P M, 2001 (Supra)]. Several markers have been recently suggested as non-invasive diagnostic tools. These include proteins [e.g., fecal calprotectin, lactoferrin, lysozyme, albumin, alpha-1-antitrypsin, carcinoembryonic antigen (CEA), decay-accelerating factor (DAF), minichrosomal maintenance protein (MCM2)] or mRNA (e.g., fecal COX-2) which can be detected in stool samples, and proteins such as nicotinamide N-methyltransferase (NNMT) or proteasome activator complex subunit 3 (PSME3) which can be detected in serum samples. However, due to their low sensitivity and specificity, these markers are not in clinical use. Other diagnostic methods such as digital rectal exam (DRE), PET-CT (positron emission tomograpgy) and virtual colonoscopy exhibit limited specificity and/or sensitivity. Thus, to date, the diagnosis of CRC is based on invasive procedures such as colon endoscopy (colonoscopy or sigmoidoscopy) followed by surgical removal of adenomas and histological staining.

CD24 is a heavily glycosilated phosphatidylinositol-anchored mucin-like cell-surface protein which is expressed mainly on hematopoietic subpopulations of B lymphocytes, various epithelial cells, muscle and neural cells. It is over-expressed in various malignant tissues including B-cell lymphomas, gliomas, small-cell and non-small cell lung, hepatocellular, renal cell, nasopharyngeal, bladder, uterine, epithelial ovarian, breast, prostate and pancreatic carcinomas (reviewed by Kristiansen et al., 2004). Moreover, its expression is correlated with increased growth rate, motility and survival of carcinoma cell lines derived from several organs (Baumann P, et al., 2005; Smith S C, et al., 2006) and with a more aggressive course of cancer. In addition, Weichert W., et al. (2005) found that increased expression of CD24 in the cytoplasm correlates with higher tumor stage, grade and presence of metastasis and concluded that over-expression of CD24 in the cytoplasm (as a result of overproduction or disturbances in distribution in the cell) is a marker for poorer prognosis. In addition, CD24 role in platelet aggregation may explain its involvement with cancer metastases and worse prognosis (Sammar, M., et al., 1994; Aigner, S., et al., 1997; Aigner, S., et al., 1998).

U.S. Pat. Appl. 20040005596 to Li J., et al., discloses methods of diagnosing cancer by determining the level of CD24 in situ in samples obtained from suspected precancerous or cancerous tissues, thus again necessitating invasional procedures for cancer detection.

While reducing the present invention to practice, the present inventors have uncovered that CD24 is over-expressed in pre-malignant lesions of the gastrointestinal tract and that shedded, blebbed or secreted CD24 can be detected in biological samples of subjects having pre-malignant and malignant lesions.

As is shown in the Examples section which follows, the present inventors have uncovered that the level of the CD24 transcript is upregulated in ras mutant-transformed cell lines (Example 1) and that its level is reversed to normal following treatment of such cells with Celecoxib, a specific COX-2 inhibitor. In addition, the present inventors have uncovered that the level of expression of CD24 in various CRC cell lines correlates with the genotype of the Val57Ala SNP in CD24, such that cells which express high level of the CD24 protein carry the $CD24^{v/v}$ genotype (Val-57 polymorph) whereas, cells that barely express the protein carry the $CD24^{a/a}$ genotype (Ala-57 polymorph) (Example 3). In addition, the present inventors have uncovered that CD24 is over-expressed in pre-malignant lesions of the GI tract which correlate with early stages of carcinogenesis (Table 1, Example 2).

Moreover, as is further illustrated in the Examples section which follows, the present inventors have shown that soluble, shedded, blebbed or secreted CD24 can be detected in serum (FIGS. 3 and 5, Example 4), stool (FIGS. 2a-c, Example 4) and urine samples of patients with CRC carcinogenesis or pre-malignant lesions of the colon-rectal and that the level of CD24 in the stool decreases following the removal (e.g., by surgery) of the pre-malignant or malignant lesions (FIGS. 2a-c) as well as when the CRC is non-active (e.g., after radiation therapy; FIGS. 2b and 3, Example 4). Altogether, these results demonstrate that CD24 is an excellent marker for early diagnosis of cancer, even at the pre-malignant stage and that soluble CD24 (e.g., secreted), blebbed and/or shedded CD24 can be detected in biological samples such as stool, serum and urine and thus be used in cancer diagnosis.

Thus, according to one aspect of present invention there is provided a method of diagnosing cancer and/or a pre-malignant lesion. The method is effected by determining a presence and/or level of a circulating CD24 of a subject in need thereof, wherein the presence and/or the level of said circulating CD24 above a predetermined threshold is indicative of the cancer and/or the pre-malignant lesion.

As used herein the phrase "pre-malignant lesion" refers to a mass of cells and/or tissue having increased probability of transforming into a malignant tumor. Preferably, in the pre-malignant lesion of the present invention CD24 is over-expressed as compared to a non-malignant tissue or cell. Examples of pre-malignant lesions include, but are not limited to, adenomatous polyps, Barrett's esophagus, IPMN (Intraductal Papillary Mucinus Neoplasia), DCIS (Ductal Carcinoma in Situ) in the breast, leukoplakia and erythroplakia. Thus, the pre-malignant lesion which is diagnosed according to the method of this aspect of the present invention can transform into a malignant solid or non-solid (e.g., hematological malignancies) CD24-associated cancer (or tumor). Preferably, the pre-malignant lesion which is diagnosed by the method of this aspect of the present invention is an adenomatous polyp of the colon, an adenomatous polyp of the rectum, an adenomatous polyp of the small bowel and Barrett's esophagus.

Non-limiting examples of CD24-associated cancers which can be diagnosed by the method of this aspect of the present invention include tumors of the gastrointestinal tract (colon cancer, rectum cancer, anal region cancer, colorectal cancer, small and/or large bowel cancer, esophageal cancer, stomach cancer, pancreatic cancer, gastric cancer, small intestine cancer, adenocarcinoma arising in the small intestine, carcinoid tumors arising in the small intestine, lymphoma arising in the small intestine, mesenchymal tumors arising in the small intestine, gastrointestinal stromal tumors), gallbladder carcinoma, Biliary tract tumors, prostate cancer, kidney (renal) cancer (e.g., Wilms' tumor), liver cancer (e.g., hepatoblastoma, hepatocellular carcinoma), hepatobiliary cancer, biliary tree cancer, tumors of the Gallbladder, bladder cancer, embryonal rhabdomyosarcoma, germ cell tumor, trophoblastic tumor, testicular germ cells tumor, immature teratoma of ovary, uterine, epithelial ovarian, sacrococcygeal tumor, choriocarcinoma, placental site trophoblastic tumor, epithelial adult tumor, ovarian cancer, cervical cancer, cancer of the vagina, cancer of the Vulva, lung cancer (e.g., small-cell and non-small cell lung carcinoma), nasopharyngeal, breast cancer, squamous cell carcinoma (e.g., in head and neck), neurogenic tumor, astrocytoma, ganglioblastoma, neuroblastoma, lymphomas (e.g., Hodgkin's disease, non-Hodgkin's lymphoma, B cell, Burkitt, cutaneous T cell, histiocytic, lymphoblastic, T cell, thymic, cutaneous T-cell lymphoma, primary central nervous system lymphoma), gliomas, medullary thyroid carcinoma, testicular cancer, brain and head/neck cancer, gynecologig cancer, endometrial cancer, germ cell tumors, mesenchymal tumors, neurogenic tumors, cancer of the bladder, cancer of the ureter, cancer of the renal pelvis, cancer of the urethra, cancer of the penis, cancer of the testis, cancers of the uterine body, endometrial carcinoma, uterine sarcoma, peritoneal carcinoma and Fallopian Tube carcinoma, germ cell tumors of the ovary, sex cord-stromal tumors, cancer of the endocrine system, thyroid tumors, medullary thyroid carcinoma, thyroid lymphoma, parathyroid tumors, adrenal tumors, pancreatic endocrine tumors, sarcomas of the soft tissue and bone, benign and malignant mesothelioma, malignant peritoneal mesothelioma, malignant mesothelioma of the Tunica Vaginalis Testis, malignant mesothelioma of the Pericardium, skin cancer, cutaneous melanoma, intraocular melanoma, neoplasms of the central nervous system, medulloblastomas, meningiomas, peripheral nerve tumors, Pineal region tumors, pituitary adenomas, craniopharyngiomas, acoustic neuromas, Glomus Jugulare tumors, Chordomas and Chondrosarcomas, Hemangioblastomas, Choroid Plexus Papillomas and Carcinomas, spinal axis tumors, leukemia, and chronic leukemia.

As used herein the phrase "diagnosing" refers to classifying a pathology (e.g., a CD24-associated cancer or a pre-malignant lesion) or a symptom, determining a severity of the pathology, monitoring pathology progression, forecasting an outcome of a pathology and/or prospects of recovery.

As used herein the phrase "subject in need thereof" refers to a human subject who is at risk of having cancer [e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness]. Additionally or alternatively, the subject in need thereof can be a healthy human subject undergoing a routine well-being check up.

As used herein the term "CD24" refers to the nucleic acid sequence and/or the amino acid sequence of at least a functional portion of the phosphatidylinositol-anchored mucin-like cell-surface protein (e.g., CD24 protein—SEQ ID NO:2, GenBank Accession No. NP_037362.1; CD24 transcript—SEQ ID NO:1, GenBank Accession No. NM_013230.2) encoded by a genomic sequence on chromosome 6q21.

The phrase "circulating CD24" refers to any CD24 molecule present in a biological sample of the subject which is not in situ anchored CD24. The phrase "in situ anchored CD24" refers to a tissue anchored CD24 amino acid or nucleic acid sequence which is anchored to intact cells at the site where it is produced (in situ) such as cells of pre-malignant lesions (e.g., adenomas) or cancerous tumors as described hereinabove. Thus, the phrase "circulating CD24" refers to any CD24 molecule which can be systemically detected. The circulating CD24 can be in a soluble or a non-soluble form (membrane anchored through a GPI moiety). Examples of such circulating CD24 include but are not limited to secreted CD24 (e.g., CD24 splice variant), shedded CD24 which is devoid of membrane components (e.g., by the action of phospholipases such as PIPLC; e.g., the amino acid sequence 27-80 of SEQ ID NO:2), blebbed CD24 (i.e., CD24 present in cell blebs that are formed by rupture of the plasma membrane from the underlying cytoskeleton followed by inflation of the detached membrane by intracellular fluid) or CD24 which is present on shedded cells (i.e., cells which are detached from the tissue).

Thus, the circulating CD24 of the present invention can be present in a biological sample that is remote from the cancerous tissue or cancer-free. For example, the biological sample may be stool, serum or urine while the cancer may be a GI cancer such as CRC.

The phrase "biological sample" as used herein refers to any cellular or non-cellular biological samples which may contain a circulating CD24 as described above. Examples include but are not limited to, a blood sample (e.g., serum), a saliva sample, a stool sample, a urine sample, pup smear, cervix sample, a bone marrow sample (specifically containing macrophages), lymph fluid, a skin sample, epithelial cells, various external secretions of the respiratory, intestinal, and genitourinary tracts, tears, milk, a tissue biopsy, a cerebrospinal fluid (CSF) sample, a sperm fluid sample, amniotic fluid, and chorionic villi sample (CVS), a sample of neuronal cells, dendritic cells, organs, and also samples of in vivo cell culture constituents.

Preferably, the biological sample used by the method of this aspect of the present invention is a blood sample (e.g., serum), a stool sample and/or a urine sample.

The biological sample can be obtained using methods known in the art such as using a syringe with a needle, a scalpel, fine needle aspiration (FNA), catheter, gastrointestinal endoscopy (e.g., colorectal endoscopy, gastro-endoscopy) and the like. Preferably, the biological sample of the present invention can be obtained by blood sampling, stool collection or urine collection. Determining the level and/or presence of soluble CD24 can be effected ex vivo (on a sample derived from the subject) as well as in vivo (within the subject).

As used herein, the phrase "presence and/or level of a circulating CD24" refers to the degree of gene expression and/or gene product activity of the CD24 gene in a biological sample. Accordingly, the presence and/or level of CD24 can be determined at the amino acid level using protein detection methods.

Thus, the presence and/or level of the CD24 amino acid sequence (CD24 protein) can be determined using a CD24 specific antibody via the formation of an immunocomplex [i.e., a complex formed between the CD24 antigen (a CD24 amino acid sequence) present in the biological sample and the CD24 specific antibody].

The immunocomplex of the present invention can be formed at a variety of temperatures, salt concentration and pH values which may vary depending on the method and the biological sample used and those of skills in the art are capable of adjusting the conditions suitable for the formation of each immunocomplex.

The term "antibody" as used in this invention includes intact molecules as well as functional fragments thereof, such as Fab, F(ab')2, Fv or single domain molecules such as VH and VL to an epitope of an antigen. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; (5) Single chain antibody ("SCA"), a genetically engineered molecule containing the variable region of the light chain and the variable region of the heavy chain, linked by a suitable polypeptide linker as a genetically fused single chain molecule; and (6) Single domain antibodies are composed of a single VH or VL domains which exhibit sufficient affinity to the antigen.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (scFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing scFvs are described, for example, by Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10,: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

According to the method of this aspect of the present invention, detection of immunocomplex formation is indicative of a diagnosis of the cancer or the pre-malignant lesion. Various methods can be used to detect the formation of the CD24 immunocomplex of the present invention and those of skills in the art are capable of determining which method is suitable for each immunocomplex and/or the type of cells used for diagnosis.

The CD24 antibody used in the immunocomplex of the present invention can be labeled using methods known in the art. It will be appreciated that the labeled antibodies can be either primary antibodies (i.e., which bind to the specific antigen, e.g., a CD24-specific antigen) or secondary antibodies (e.g., labeled goat anti rabbit antibodies, labeled mouse anti human antibody) which bind to the primary antibodies. The antibody can be directly conjugated to a label or can be conjugated to an enzyme.

Antibodies of the present invention can be fluorescently labeled (using a fluorescent dye conjugated to an antibody), radiolabeled (using radiolabeled e.g., $I^{125}$, antibodies), or conjugated to an enzyme (e.g., horseradish peroxidase or alkaline phosphatase) and used along with a chromogenic substrate to produce a colorimetric reaction. The chromogenic substrates utilized by the enzyme-conjugated antibodies of the present invention include, but are not limited to, AEC, Fast red, ELF-97 substrate [2-(5'-chloro-2-phosphoryloxyphenyl)-6-chloro-4(3H)-quinazolinone], p-nitrophenyl phosphate (PNPP), phenolphthalein diphosphate, and ELF 39-phosphate, BCIP/INT, Vector Red (VR), salmon and magenta phosphate (Avivi C., et al., 1994, J. Histochem. Cytochem. 1994; 42: 551-4) for alkaline phosphatase enzyme and Nova Red, diaminobenzidine (DAB), Vector(R) SG substrate, luminol-based chemiluminescent substrate for the peroxidase enzyme. These enzymatic substrates are commercially available from Sigma (St Louis, Mo., USA), Molecular Probes Inc. (Eugene, OR, USA), Vector Laboratories Inc. (Burlingame, CA, USA), Zymed Laboratories Inc. (San Francisco, CA, USA), Dako Cytomation (Denmark).

Detection of the CD24 immunocomplex in a biological sample such as serum, stool or urine which may contain circulating CD24 can be performed using fluorescence activated cell sorting (FACS), enzyme linked immunosorbent assay (ELISA), Western blot and radio-immunoassay (RIA) analyses, immunoprecipitation (IP) or by a molecular weight-based approach.

For Western blot the proteins are extracted from a cell sample and are subjected to electrophoresis (e.g., SDS-PAGE) and blotting to a membrane (e.g., nylon or PVDF). The membrane is then interacted with a CD24 antibody which can be either directly labeled or further subjected to a secondary labeled antibody. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

In case the concentration of the antigen in the biological sample is low, detection of the antigen (CD24 amino acid sequence) can be performed by immunoprecipitation (IP), essentially as described in the Examples section which follows. For immunoprecipitation analysis the CD24 antibody may directly interact with a sample (e.g., cell lysate) including CD24 and the formed complex can be further detected using a secondary antibody conjugated to beads (e.g., if the CD24 antibody is a mouse monoclonal antibody, the secondary antibody may be an anti-mouse antibody conjugated to e.g., Sepharose beads). The beads can be then precipitated by centrifugation, following which the precipitated proteins (e.g., CD24 and anti CD24 antibodies) can be detached from the beads (e.g., using denaturation at 95° C.) and further subjected to Western blot analysis using the CD24 specific antibodies. Alternatively, the anti-CD24 antibody and the beads-conjugated secondary antibody may be added to the biological sample containing the antigen (CD24) to thereby form an immunocomplex. Alternatively, since CD24 is a highly glycosilated protein, it can be also precipitated using a substrate capable of binding glycosilated polypeptides such Concavalin A (GE Healthcare Bio-Sciences, Uppsala, Sweden) which may be also conjugated to beads, followed by Western blot analysis with anti-CD24 antibodies.

FACS analysis enables the detection of antigens present on cell membranes such as CD24. Briefly, CD24 specific antibodies are linked to fluorophores and detection is performed by means of a cell sorting machine which reads the wavelength of light emitted from each cell as it passes through a light beam. This method may employ two or more antibodies simultaneously.

The presence and/or level of CD24 can be also determined using ELISA. Briefly, a sample containing CD24 antigen is fixed to a surface such as a well of a microtiter plate. An antigen specific antibody (a CD24 antibody) coupled to an enzyme is applied and allowed to bind to the antigen. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

The presence and/or level of CD24 can be also determined using radio-immunoassay (RIA). In one version, this method involves precipitation of the desired antigen (CD24) with a specific antibody and radiolabeled antibody binding protein (e.g., protein A labeled with $I^{125}$) immobilized on a precipitable carrier such as agarose beads. The number of counts in the precipitated pellet is proportional to the amount of antigen.

In an alternate version of the RIA, a labeled antigen and an unlabelled antibody binding protein are employed. A sample containing an unknown amount of antigen is added in varying amounts. The decrease in precipitated counts from the labeled antigen is proportional to the amount of antigen in the added sample.

The presence and/or level of CD24 can be also determined using molecular weight-based approach. Since the immunocomplex exhibits a higher molecular weight than its components, methods capable of detecting such a change in the molecular weight can be also employed. For example, the immunocomplex can be detected by a gel retardation assay. Briefly, a non-denaturing acrylamide gel is loaded with samples. A shift in the size (molecular weight) of the protein product as compared with its components is indicative of the presence of an immunocomplex. Such a shift to a higher molecular weight can be viewed using a non-specific protein staining such as silver stain or Commassie blue stain.

It will be appreciated that since shedded cells or fragments thereof (also referred to as blebbed) may also include mRNA molecules, detection of the circulating CD24 in the biological sample may be also performed using mRNA detection methods which are capable of detecting CD24 over expression. In cases of DNA amplification of the gene, detection of circulating CD24 can also be effected at the DNA level in the biological sample.

RNA or DNA detection methods can be performed using an isolated polynucleotide (e.g., a polynucleotide probe, an oligonucleotide probe/primer) capable of hybridizing to a CD24 nucleic acid sequence such as the CD24 transcript set forth by SEQ ID NO:1 or a portion thereof. Such a polynucleotide can be at any size, such as a short polynucleotide (e.g., of 15-200 bases), an intermediate polynucleotide of 100-2000 bases and a long polynucleotide of more than 2000 bases.

The isolated polynucleotide probe used by the present invention can be any directly or indirectly labeled RNA molecule [e.g., RNA oligonucleotide (e.g., of 17-50 bases), an in vitro transcribed RNA molecule], DNA molecule (e.g., oligonucleotide, e.g., 15-50 bases, cDNA molecule, genomic molecule) and/or an analogue thereof [e.g., peptide nucleic acid (PNA)] which is specific to the CD24 RNA transcript of the present invention.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The isolated polynucleotide used by the present invention can be labeled either directly or indirectly using a tag or label molecule. Such labels can be, for example, fluorescent molecules (e.g., fluorescein or Texas Red), radioactive molecule (e.g., $^{32}P$-γ-ATP or $^{32}P$-α-ATP) and chromogenic substrates [e.g., Fast Red, BCIP/INT, available from (ABCAM, Cambridge, Mass.)]. Direct labeling can be achieved by covalently conjugating a label molecule to the polynucleotide (e.g., using solid-phase synthesis) or by incorporation via polymerization (e.g., using an in vitro transcription reaction or random-primed labeling). Indirect labeling can be achieved by covalently conjugating or incorporating to the polynucleotide a non-labeled tag molecule (e.g., Digoxigenin or biotin) and subsequently subjecting the polynucleotide to a labeled molecule (e.g., anti-Digoxigenin antibody or streptavidin) capable of specifically recognizing the non-labeled tag.

The above-described polynucleotides can be employed in a variety of RNA detection methods such as Northern blot analysis, reverse-transcribed PCR(RT-PCR) [e.g., a semi-quantitative RT-PCR, quantitative RT-PCR using e.g., the Light Cycler™ (Roche)], RNA in situ hybridization (RNA-ISH), in situ RT-PCR stain [e.g., as described in Nuovo G J, et al. 1993, Intracellular localization of polymerase chain reaction (PCR)-amplified hepatitis C cDNA. Am J Surg Pathol. 17: 683-90, and Komminoth P, et al. 1994, Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract., 190: 1017-25] and oligonucleotide microarray analysis [e.g., using the Affymetrix microarray (Affymetrix®, Santa Clara, CA)].

DNA detection methods which can be used along with the present invention include, but are not limited to, Southern blot analysis, PCR, quantitative PCR and restriction fragment length polymorphism (RFLP).

As used herein the phrase "predetermined threshold" refers to a known level of circulating CD24 in a sample. Such a level can be experimentally determined by comparing normal samples (e.g., samples obtained from healthy subjects) to samples derived from subjects known to have carcinogenesis such as CRC (see for example, Table 1 and Example 2 of the Examples section which follows). Alternatively, such a level can be obtained from the scientific literature.

Thus, the presence and/or the level of the CD24 in the biological sample above a predetermined threshold is indicative of the cancer or the pre-malignant lesion.

It will be appreciated that the presence of the cancer or the pre-malignant lesion can be further validated using additional assays. For example, in case the level of CD24 detected in the stool of a subject is above a predetermined threshold, additional assays such as colon endoscopy followed by histological evaluations (including CD24 immunostaining) may be performed on the identified adenomas (in case adenomas are present).

Thus, the teachings of the present invention provide, for the first time, a highly reliable (over 80% accuracy), non-invasive method of diagnosing pre-malignant or malignant lesions of the gastrointestinal tract using biological samples such as serum, urine and stool.

It will be appreciated that the teachings of the present invention can be further used to monitor efficacy of cancer therapy or disease progression/remission. As is shown in FIG. 2b and described in Example 4 of the Examples section which follows, the level of CD24 in the stool decreased following radiation therapy in a subject suffering from CRC, probably as a result of a significant reduction in cancerous cells in the subject.

Thus, according to another aspect of the present invention there is provided a method of monitoring efficacy of cancer therapy. The method is effected by determining a level of a circulating CD24 in a biological sample of the subject following the cancer therapy, wherein a decrease from a predetermined threshold in the level of the circulating CD24 following the cancer therapy is indicative of reduction of cancerous cells, thereby monitoring efficacy of the cancer therapy.

The cancer therapy which efficacy is monitored according to the method of this aspect of the present invention can be radiation therapy, chemotherapy (e.g., CHOP, Cisplatin, carboplatin, oxaliplatin, azathioprine, mercaptopurine, vinca alkaloids, etoposide, teniposide, paclitaxel, docetaxel, irinotecan, topotecanamsacrine, etoposide, etoposide phosphate, teniposide and dactinomycin), antibody therapy [e.g., trastuzumab (Herceptin) and rituximab (Rituxan)] or a combination of any of the above.

Thus, a decrease from a pre-determined threshold in the level of circulating CD24 is indicative of the cancer therapy being efficient. On the other hand, if there is no decrease, or in case there is an increase from the pre-determined threshold in the level of circulating CD24 after treatment, then the cancer therapy is not efficient in eliminating (e.g., killing, depleting) the cancerous cells from the treated subject and additional and/or alternative therapies (e.g., treatment regimens) may be used.

It will be appreciated that the pre-determined threshold can be determined in a subset of subjects with known outcome of therapy.

Preferably, the decrease from the pre-determined threshold is of at least 10 times, more preferably, 15 times, preferably, 20 times, preferably, 50 times or at least 100 times (e.g., at least 1000 times) in the level of circulating CD24 following cancer therapy.

While further reducing the present invention to practice, the present inventors have uncovered that polymorphisms in the CD24 gene may be used as markers for predisposition of a subject to gastrointestinal cancer.

Figure 4:
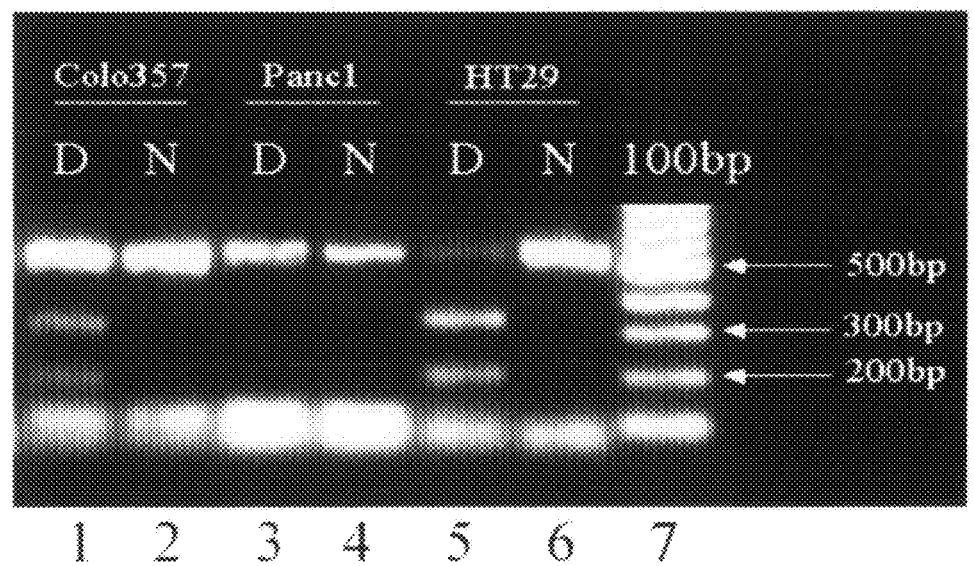
FIG. 4 is an RFLP analysis of the Val57Ala polymorphism in the CD24 protein (SEQ ID NO:2) (C/T at position 280 of SEQ ID NO:1). Genomic DNA was subjected to PCR amplification using the forward (SEQ ID NO:3) and reverse (SEQ ID NO:4) primers and the resultant 520 by PCR products were either digested using the BstXI restriction enzyme ("D" for digested, lanes 1, 3, and 5) or remained non-digested ("N" for non-digested, lanes 2, 4 and 6) and electrophoressed on a 1% agarose gel. Lanes 1 and 2—DNA of the colo357 pancreatic cancer cell line, which expresses high levels of CD24; lanes 3 and 4—DNA of the Panel pancreatic cancer cell line, which expresses moderate levels of CD24; lanes 5 and 6—DNA of the HT29 colon cancer cell line which expresses high levels of CD24; lane 7—100 by molecular weight marker. Note that while Panc1 cells which express moderate levels of CD24 exhibit the C/C genotype at position 280 of SEQ ID NO:1 (which corresponds to the Ala polymorph at position 57 of SEQ ID NO:2) as is evidenced by the presence of only the undigested PCR product of 520 bp, the colo357 or HT29 cells, which express high levels of CD24 exhibit the C/T or the TT genotypes at position 280 of SEQ ID NO:1 (corresponding to the Ala/Val or Val/Val polymorphs at position 57), respectively, as is evidenced by the presence of both digested and undigested PCR products in lane 1 (Colo357) and only the digested PCR products in lane 5 (HT29).

As is shown in Table 2, FIG. 4 and described in Example 3 of the Examples section which follows, individuals who carry the Val polymorph at position 57 of the CD24 protein (SEQ ID NO:2) have increased predisposition risk to develop gastrointestinal cancer. In addition, as is further illustrated in Example 3 of the Examples section which follows individuals who carry the Val polymorph at position 57 of the CD24 protein (SEQ ID NO:2) as well as the 1317Q and/or the 1307K polymorph of APC (SEQ ID NO:8) have increased predisposition risk to develop gastrointestinal cancer. These results suggest the use of the combination of the Val/Ala polymorphism at position 57 of the CD24 protein and the E1317Q and/or I1307K of the APC protein for determining predisposition to gastrointestinal cancer.

Thus, according to another aspect of the present invention there is provided a method of determining if a subject is predisposed to gastrointestinal cancer. The method is effected by determining a presence or absence, in a homozygous or heterozygous form, of at least one cancer-associated genotype in the CD24 nucleic acid sequence of the subject, thereby determining if the subject is predisposed to the gastrointestinal cancer.

As used herein, the term "predisposed" when used with respect to gastrointestinal cancer refers to a subject who is more susceptible to developing gastrointestinal cancer than non-predisposed subjects.

The terms "homozygous" or "heterozygous" refer to two identical or two different alleles, respectively, of a certain polymorphism.

The term "polymorphism" refers to the occurrence of two or more genetically determined variant forms (alleles) of a particular nucleic acid at a frequency where the rarer (or rarest) form could not be maintained by recurrent mutation alone. A single nucleotide polymorphism (SNP) results from a single base difference between related alleles at the same genetic locus. A non-limiting example of a polymorphism is the presence of a cytosine or thymidine nucleotide at position 280 of CD24 coding sequence (SEQ ID NO:1; GenBank Accession No. NM_013230.2) which results in a non-synonymous missense mutation of Ala/Val at position 57 of the CD24 polypeptide (SEQ ID NO:2; GenBank Accession No. NP_037362.1).

The term "absence" as used herein in regard to the genotype describes the negative result of a specific genotype determination test. For example, if the genotype determination test is suitable for the identification of thymidine nucleotide containing allele at position 280 of SEQ ID NO:1, and the subject on which the test is performed is homozygote for the cytosine nucleotide—containing allele at position 280 of SEQ ID NO:1, then the result of the test will be "absence of genotype".

Preferably, the at least one cancer-associated genotype in the CD24 nucleic acid sequence is a thymidine nucleotide containing allele at position 280 of the polynucleotide set forth by SEQ ID NO:1.

As is further shown in Example 3 of the Examples section which follows, the present inventors have uncovered that individuals carrying both the thymidine nucleotide containing allele at position 280 of the polynucleotide set forth by SEQ ID NO:1 (which encodes the Val-57 polymorph of CD24) and the adenosine nucleotide containing allele at position 3977 of the polynucleotide set forth by SEQ ID NO:7 [which encodes the Lys (K)-1307 polymorph of APC] and/or the cytosine nucleotide containing allele at position 4006 of the polynucleotide set forth by SEQ ID NO:7 [which encodes the Gln (Q)-1317 polymorph of APC) have increased predisposition to gastrointestinal cancer [p-values are 0.024 for Val-57 and Lys (K)-1307 and 0.028 for Val-57 and Gln (Q)-1317].

Thus, according to preferred embodiments of the present invention the method of determining if a subject is predisposed to gastrointestinal cancer further comprising determining a presence or an absence, in a homozygous or heterozygous form, of at least one cancer-associated genotype in an APC nucleic acid sequence of the subject.

Preferably, the at least one cancer-associated genotype in the APC nucleic acid sequence is an adenosine nucleotide containing allele at position 3977 of the polynucleotide set forth by SEQ ID NO:7 (which encodes the lysine-1307 polymorph of the APC polypeptide set forth by SEQ ID NO:8).

Preferably, the at least one cancer-associated genotype in the APC nucleic acid sequence is an cytosine nucleotide containing allele at position 4006 of the polynucleotide set forth by SEQ ID NO:7 (which encodes the Glutamine-1317 of the polypeptide set forth by SEQ ID NO:8).

Preferably, the at least one cancer-associated genotype in the APC nucleic acid sequence is an adenosine nucleotide containing allele at position 3977 and a cytosine nucleotide containing allele at position 4006 of the polynucleotide set forth by SEQ ID NO:7.

The predisposition to gastrointestinal cancer can be quantified by generating and using genotype relative risk (GRR) values. The GRR is the increased chance of an individual with a particular genotype to develop the disease. Thus, the GRR of the risk genotype G, with respect to the protective genotype $G_0$, is the ratio between the risk of an individual carrying genotype G to develop the disease, and the risk of an individual carrying genotype $G_0$ to develop the disease (e.g., CRC). The GRR used herein is represented in terms of an appropriate odds ratio (OR) of G versus $G_0$ in cases and controls. Moreover, computation of GRR of haplotypes is based on a multiplicative model in which the GRR of an homozygote individual is the square of the GRR of an heterozygote individual. For further details see Risch and Merikangas, 1996 [The future of genetic studies of complex human diseases. Science 273: 1516-1517].

Once calculated, the GRR can reflect the increased predisposition risk of an individual with a specific cancer-associated genotype in the CD24 nucleic acid sequence and/or the APC nucleic acid sequence to develop gastrointestinal cancer.

Thus, the present invention provides a method of predicting predisposition of a subject to gastrointestinal cancer by detecting specific genotypes in the CD24 and APC genes and/or proteins. It will be appreciated that such genotypes can be detected on the DNA level, as well as on the protein level using antibodies capable of detecting specific protein polymorphs.

A DNA or a protein sample can be obtained from any source of cells or cell content of the subject, including, but not limited to, peripheral blood cells (obtained using a syringe, e.g., white blood cells), skin cells (obtained from a skin biopsy), mouth epithelial cells (obtained from a mouth wash), cerebrospinal fluid, urine, lymph fluids, various external secretions of the respiratory, intestinal, and genitourinary tracts, tears, saliva, and milk, as well as malignant tissues, amniotic fluid, and chorionic villi, tissue sections (e.g., frozen sections or paraffin-embedded sections) and the like.

Once the sample is obtained, DNA is preferably extracted using methods which are well known in the art, involving tissue mincing, cell lysis, protein extraction, and DNA precipitation using 2 to 3 volumes of 100% ethanol, rinsing in 70% ethanol, pelleting, drying, and resuspension in water or any other suitable buffer (e.g., Tris-EDTA). Preferably, following such a procedure, DNA concentration is determined, such as by measuring the optical density (OD) of the sample at 260 nm (wherein 1 unit OD=50 µg/ml DNA). Alternatively, DNA can be obtained by adding a protein digestion enzyme (e.g., proteinase K), followed by denaturation (e.g., boiling at 95° C. for 5-10 minutes). Still alternatively, DNA can be isolated from tissue sections (e.g., archive paraffin embedded sections) as described previously (Arber N, Shapira I, et al., 2000, Activation of c-K-ras mutations in human gastrointestinal tumors. Gastroenterology, 118: 1045-50).

Preferably, the DNA sample is obtained from a peripheral blood sample. Methods of extracting DNA from blood samples are well known in the art.

Once obtained, the DNA sample is preferably characterized for the presence or absence of at least one or more of the cancer-associated genotype in the CD24 and/or APC nucleic acid sequence of the present invention.

The SNPs of the present invention can be identified using a variety of approaches suitable for identifying sequence alterations. One option is to determine the entire gene sequence of a PCR reaction product. Alternatively, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

The DNA sample is preferably amplified prior to determining sequence alterations, since many genotyping methods require amplification of the DNA region carrying the sequence alteration of interest.

In any case, the presence of a sequence alteration (e.g., SNP) in the CD24 or APC genes is determined using methods which typically involve the use of oligonucleotides that specifically hybridize with the nucleic acid sequence alterations in the CD24 or APC genes, such as those described hereinabove.

The term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly to respective naturally-occurring portions.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The oligonucleotide of the present invention is of at least 17, at least 18, at least 19, at least 20, at least 22, at least 25, at least 30 or at least 40, bases specifically hybridizable with sequence alterations described hereinabove.

The oligonucleotides of the present invention may comprise heterocylic nucleosides consisting of purines and the pyrimidines bases, bonded in a 3' to 5' phosphodiester linkage.

Preferably used oligonucleotides are those modified in either backbone, internucleoside linkages or bases, as is known in the art.

Following is a non-limiting list of SNPs detection methods which can be used to identify one or more of the SNPs described above.

Restriction fragment length polymorphism (RFLP)—This method utilizes a change in a single nucleotide (the SNP nucleotide) that modifies a recognition site for a restriction enzyme, resulting in the creation or destruction of an RFLP. Single nucleotide mismatches in DNA heteroduplexes are also recognized and cleaved by some chemicals, providing an alternative strategy to detect single-base substitutions, generically named the "Mismatch Chemical Cleavage" (MCC) (Gogos, J. A. et al. (1990). Detection of single base mismatches of thymine and cytosine residues by potassium permanganate and hydroxylamine in the presence of tetralkylammonium salts. Nucl Acids Res 18, 6807-6814). However, this method requires the use of osmium tetroxide and piperidine, two highly noxious chemicals that are not suited for use in a clinical laboratory.

Sequencing analysis—The isolated DNA is subjected to automated dideoxy terminator sequencing reactions using a dye-terminator (unlabeled primers and labeled dideoxy nucleotides) or a dye-primer (labeled primers and unlabeled dideoxy nucleotides) cycle sequencing protocol. For the dye-terminator reaction, a PCR reaction is performed using unlabeled PCR primers, followed by a sequencing reaction in the presence of one of the primers, deoxynucleotides, and the labeled dideoxy nucleotide mix. For the dye-primer reaction, a PCR reaction is performed using PCR primers conjugated to universal or reverse primers (one in each direction), followed by a sequencing reaction in the presence of four separate mixes (corresponding to the A, G, C, and T nucleotides), each containing a labeled primer specific to the universal or reverse sequence, and the corresponding unlabeled dideoxy nucleotides.

Microsequencing analysis—This analysis can be effected by conducting microsequencing reactions on specific regions of the CD24 or APC genes which may be obtained by amplification reaction (PCR), as mentioned hereinabove. Genomic or cDNA amplification products are then subjected to automated microsequencing reactions using ddNTPs (using specific fluorescence for each ddNTP) and an appropriate oligonucleotide microsequencing primer which can hybridize just upstream of the alteration site of interest. Once specifically extended at the 3' end by a DNA polymerase using a complementary fluorescent dideoxynucleotide analogue (e.g., via thermal cycling), the primer is precipitated to remove the unincorporated fluorescent ddNTPs. The reaction products into which fluorescent ddNTPs have been incorporated are then analyzed by electrophoresis on sequencing machines (e.g., ABI 377) to determine the identity of the incorporated base, thereby identifying the sequence alteration in the CD24 or APC genes of the present invention.

It will be appreciated that the extended primer may also be analyzed by MALDI-TOF Mass Spectrometry. In this case, the base at the alteration site is identified by the mass added onto the microsequencing primer. (See Haff, L. A. and Smirnov, I. P. (1997). Multiplex genotyping of PCR products with MassTag-labeled primers, Nucl Acids Res 25(18), 3749-3750.)

Recently developed solid-phase microsequencing reactions can be utilized as an alternative to the microsequencing approach described hereinabove. Solid-phase microsequencing reactions employ oligonucleotide microsequencing primers or PCR-amplified products of the DNA fragment of interest, which are immobilized. Immobilization can be carried out, for example, via an interaction between biotinylated DNA and streptavidin-coated microtitration wells or avidin-coated polystyrene particles.

In solid-phase microsequencing reactions, incorporated ddNTPs can be either radiolabeled (Syvanen, A. C. (1994). Detection of point mutations in human genes by the solid-phase minisequencing method. Clin Chim Acta 226, 225-236) or linked to fluorescein (Livak, K. J. and Hainer, J. W. (1994). A microtiter plate assay for determining apolipoprotein E genotype and discovery of a rare allele. Hum Mutat 3(4), 379-385). The detection of radiolabeled ddNTPs can be achieved through scintillation-based techniques. The detection of fluorescein-linked ddNTPs is based on the binding of antifluorescein antibody conjugated with alkaline phosphatase, followed by incubation with a chromogenic substrate (such asp-nitrophenyl phosphate).

Other reporter-detection conjugates include ddNTP linked to dinitrophenyl (DNP) and anti-DNP alkaline phosphatase conjugate (see Harju, L. et al. (1993). Colorimetric solid-phase minisequencing assay for the detection of alpha-1-antitrypsin Z mutation. Clin Chem 39(2), 2282-2287) and biotinylated ddNTP and horseradish peroxidase-conjugated streptavidin with o-phenylenediamine as a substrate (see WO 92/15712).

A diagnostic kit based on fluorescein-linked ddNTP with antifluorescein antibody conjugated with alkaline phosphatase is commercially available from GamidaGen Ltd (PR-ONTO).

Other modifications of the microsequencing protocol are described by: Nyren, P. B. et al. (1993). Solid phase DNA minisequencing by an enzymatic luminometric inorganic pyrophosphate detection assay. Anal Biochem 208(1), 171-175; and Pastinen, T. et al. (1997). Minisequencing: A specific tool for DNA analysis and diagnostics on oligonucleotide arrays. Genome Research 7, 606-614.

Mismatch detection assays based on polymerases and ligases—The Oligonucleotide Ligation Assay (OLA) uses two oligonucleotides that are designed to be capable of hybridizing to abutting sequences of a single strand of a target molecule. One of the oligonucleotides is biotinylated, and the other is detectably labeled. If the precise complementary sequence is found in a target molecule, the oligonucleotides will hybridize to the target such that their termini abut, and create a ligation substrate that can be captured and detected. OLA is capable of detecting single nucleotide polymorphisms and may be advantageously combined with PCR, as described by: Nickerson, J. A. et al. (1990). Automated DNA diagnostics using an ELISA-based oligonucleotide ligation assay. Proc Natl Acad Sci U.S.A. 87, 8923-8927. In this method, PCR is used to achieve the exponential amplification of target DNA, which is then detected using OLA.

Other amplification methods which are particularly suited for the detection of single nucleotide polymorphisms include LCR (ligase chain reaction) and Gap LCR (GLCR). LCR uses two pairs of probes to exponentially amplify a specific target. The sequences of each pair of oligonucleotides are selected to permit the pair to hybridize to abutting sequences of the same strand of the target. Such hybridization forms a substrate for a template-dependant ligase. In accordance with the present invention, LCR can be performed with oligonucleotides having the proximal and distal sequences of the same strand of a biallelic marker site. In one embodiment, either oligonucleotide will be designed to include the biallelic marker site. In such an embodiment, the reaction conditions are selected such that the oligonucleotides can be ligated together only if the target molecule either contains or lacks the specific nucleotide that is complementary to the biallelic marker on the oligonucleotide. In an alternative embodiment, the oligonucleotides will not include the biallelic marker, such that when they hybridize to the target molecule, a "gap" is created, as described in WO 90/01069. This gap is then "filled" with complementary dNTPs (as mediated by DNA polymerase), or by an additional pair of oligonucleotides. Thus, at the end of each cycle, each single strand has a complement capable of serving as a target during the next amplification cycle, and exponential allele-specific amplification of the desired sequence is obtained.

Ligase/Polymerase-mediated Genetic Bit Analysis™— This is another method for determining the identity of a nucleotide at a preselected site in a nucleic acid molecule (WO 95/21271). This method involves the incorporation of a nucleoside triphosphate, which is complementary to the nucleotide present at the preselected site, onto the terminus of a primer molecule, and their subsequent ligation to a second oligonucleotide. The reaction is monitored by detecting a specific label attached to the reaction's solid phase or by detection in solution.

Hybridization assay methods—Hybridization-based assays which allow the detection of single-base alterations rely on the use of an oligonucleotide which can be 10, 15, 20, or 30 to 100 nucleotides long, preferably from 10 to 50, more preferably from 40 to 50 nucleotides in length. Typically, the oligonucleotide includes a central nucleotide complementary to a polymorphic site of the CD24 or APC genes, and flanking nucleotide sequences spanning on each side of the central nucleotide that are substantially complementary to the nucleotide sequences of the CD24 or APC genes spanning on each side of the polymorphic site. Sequence alteration can be detected by hybridization of the oligonucleotide of the present invention to the template sequence under stringent hybridization reactions.

By way of example, hybridization of short nucleic acids (below 200 bp in length, e.g. 17-40 by in length) can be effected by any of the following hybridization protocols, depending on the desired stringency: (i) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA, and 0.1% nonfat dried milk, hybridization temperature of 1-1.5° C. below the $T_m$, final wash solution of 3 M TMACl, 0.01 M sodium phosphate (pH 6.8), 1 mM EDTA (pH 7.6), and 0.5% SDS at 1-1.5° C. below the $T_m$; (ii) hybridization solution of 6×SSC and 0.1% SDS or 3 M TMACl, 0.01 M sodium phosphate (pH 6.8), 1 mM EDTA (pH 7.6), 0.5% SDS, 100 µg/ml denatured salmon sperm DNA, and 0.1% nonfat dried milk, hybridization temperature of 2-2.5° C. below the $T_m$, wash solution of 3 M TMACl, 0.01 M sodium phosphate (pH 6.8), 1 mM EDTA (pH 7.6), and 0.5% SDS at 1-1.5° C. below the $T_m$, and a final wash solution of 6×SSC at 22° C.; and (iii) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA, and 0.1% nonfat dried milk, hybridization temperature.

The detection of hybrid duplexes can be carried out by a number of methods. Typically, hybridization duplexes are separated from unhybridized nucleic acids and the labels bound to the duplexes are then detected. Such labels refer to radioactive, fluorescent, biological, or enzymatic tags or labels of standard use in the art. A label can be conjugated to either the oligonucleotide probes or the nucleic acids derived from the biological sample (target). For example, oligonucleotides of the present invention can be labeled subsequent to synthesis, by incorporating biotinylated dNTPs or rNTP, or by some similar means (e.g., photo-cross-linking a psoralen derivative of biotin to RNAs), followed by addition of labeled streptavidin (e.g., phycoerythrin-conjugated streptavidin) or the equivalent. Alternatively, when fluorescently-labeled oligonucleotide probes are used, fluorescein, lissamine, phycoerythrin, rhodamine (Perkin Elmer Cetus), Cy2, Cy3, Cy3.5, Cy5, Cy5.5, Cy7, Fluor X (Amersham), and/or others (see, e.g., Kricka, J. D. (1992), "Nonisotopic DNA Probe Techniques," Academic Press, San Diego) can be attached to the oligonucleotides.

Traditional hybridization assays include PCR, RT-PCR, RNase protection, in-situ hybridization, primer extension, Southern blot, Northern Blot, and dot blot analysis.

Those skilled in the art will appreciate that wash steps may be employed to wash away excess target DNA or probe as well as unbound conjugate. Further, standard heterogeneous assay formats are suitable for detecting the hybrids using the labels present on the oligonucleotide primers and probes.

Two recently developed assays allow hybridization-based allele discrimination with no need for separations or washes (see Landegren, U. et al. (1998). Reading bits of genetic information: methods for single-nucleotide polymorphism analysis. Genome Res 8(8), 769-776). The TaqMan® assay takes advantage of the 5' nuclease activity of Taq DNA polymerase to digest a DNA probe annealed specifically to the accumulating amplification product. TaqMan probes are labeled with a donor-acceptor dye pair that interact via fluorescence energy transfer. C1 cleavage of the TaqMan probe by the advancing polymerase during amplification dissociates the donor dye from the quenching acceptor dye, greatly increasing the donor fluorescence. All reagents necessary to detect two allelic variants can be assembled at the beginning of the reaction and the results are monitored in real time (see Livak, K. J. and Hainer, J. W. (1994). A microtiter plate assay for determining apolipoprotein E genotype and discovery of a rare allele. Hum Mutat 3(4), 379-385). In an alternative homogeneous hybridization-based procedure, molecular beacons are used for allelic discrimination. Molecular beacons are hairpin-shaped oligonucleotide probes that report the presence of specific nucleic acids in homogeneous solutions. When they bind to their targets they undergo a conformational reorganization that restores the fluorescence of an internally quenched fluorophore (Tyagi, S. et al. (1998). Multicolor molecular beacons for allele discrimination. Nat Biotechnol 16(1), 49-53).

It will be appreciated that a variety of controls may be usefully employed to improve accuracy of hybridization assays. For instance, samples may be hybridized to an irrelevant probe and treated with RNase A prior to hybridization, to assess false hybridization.

U.S. Pat. No. 5,451,503 provides several examples of oligonucleotide configurations which can be utilized to detect SNPs in template DNA or RNA.

Hybridization to oligonucleotide arrays—The chip/array technology has already been applied with success in numerous cases. For example, the screening of mutations has been undertaken in the BRCA1 gene, in *S. cerevisiae* mutant strains, and in the protease gene of HIV-1 virus (see: Hacia, J G et al. (1996). Detection of heterozygous mutations in BRCA1 using high density oligonucleotide arrays and two-colour fluorescence analysis. Nat Genet. 14(4), 441-447; Shoemaker, D. D. et al. (1996). Quantitative phenotypic analysis of yeast deletion mutants using a highly parallel molecular bar-coding strategy. Nat Genet. 14(4), 450-456; and Kozal, M. J. et al. (1996). Extensive polymorphisms observed in HIV-1 Glade B protease gene using high-density oligonucleotide arrays. Nat Med 2(7), 753-759).

The nucleic acid sample that includes the candidate region to be analyzed is isolated, amplified, and labeled with a reporter group. This reporter group can be a fluorescent group such as phycoerythrin. The labeled nucleic acid is then incubated with the probes immobilized on the chip using a fluidics station. For example, Manz et al. describe the fabrication of fluidics devices and particularly microcapillary devices, in silicon and glass substrates (Manz, A. et al. (1993). Planar chip technology for miniaturization of separation systems. Adv in Chromatogr 33, 1-66).

Once the reaction is completed, the chip is inserted into a scanner and patterns of hybridization are detected. The hybridization data is collected from a signal emitted from the reporter groups already incorporated into the nucleic acid, which is now bound to the probes attached to the chip. Probes that perfectly match a sequence of the nucleic acid sample generally produce stronger signals than those that have mismatches. Since the sequence and position of each probe immobilized on the chip is known, the identity of the nucleic acid hybridized to a given probe can be determined.

For single-nucleotide polymorphism analyses, sets of four oligonucleotide probes (one for each base type), preferably sets of two oligonucleotide probes (one for each base type of the biallelic marker), are generally designed that span each position of a portion of the candidate region found in the nucleic acid sample, differing only in the identity of the polymorphic base. The relative intensity of hybridization to each series of probes at a particular location allows the identification of the base corresponding to the polymorphic base of the probe.

It will be appreciated that the use of direct electric field control improves the determination of single base mutations (Nanogen). A positive field increases the transport rate of negatively charged nucleic acids and results in a 10-fold increase in hybridization rates. Using this technique, single base pair mismatches are detected in less than 15 seconds (see Sosnowski, R. G. et al. (1997). Rapid determination of single base mismatch mutations in DNA hybrids by direct electric field control. Proc Natl Acad Sci USA 94(4), 1119-1123).

Integrated systems—Another technique which may be used to analyze sequence alterations includes multicomponent integrated systems, which miniaturize and compartmentalize processes such as PCR and capillary electrophoresis reactions in a single functional device. An example of such a technique is disclosed in U.S. Pat. No. 5,589,136, which describes the integration of PCR amplification and capillary electrophoresis in chips.

Integrated systems are preferably employed along with microfluidic systems. These systems comprise a pattern of microchannels designed onto a glass, silicon, quartz, or plastic wafer included on a microchip. The movements of the samples are controlled by electric, electro-osmotic, or hydrostatic forces applied across different areas of the microchip, to create functional microscopic valves and pumps with no moving parts. Varying the voltage controls the liquid flow at intersections between the micro-machined channels and changes the liquid flow rate for pumping across different sections of the microchip.

When identifying sequence alterations, a microfluidic system may integrate nucleic acid amplification, microsequencing, capillary electrophoresis, and a detection method such as laser-induced fluorescence detection. In a first step, the DNA sample is amplified, preferably by PCR. The amplification product is then subjected to automated microsequencing reactions using ddNTPs (with specific fluorescence for each ddNTP) and the appropriate oligonucleotide microsequencing primers, which hybridize just upstream of the targeted polymorphic base. Once the extension at the 3' end is completed, the primers are separated from the unincorporated fluorescent ddNTPs by capillary electrophoresis. The separation medium used in capillary electrophoresis can for example be polyacrylamide, polyethylene glycol, or dextran. The incorporated ddNTPs in the single-nucleotide primer extension products are identified by fluorescence detection. This microchip can be used to process 96 to 384 samples in parallel. It can use the typical four-color laser-induced fluorescence detection of ddNTPs.

It will be appreciated that when utilized along with automated equipment, the above-described detection methods can be both rapidly and easily used to screen multiple samples for the CD24 or APC alterations of the present invention.

Allele-specific oligonucleotides (ASOs)—In this method, an allele-specific oligonucleotide (ASO) is designed to hybridize in proximity to the polymorphic nucleotide, such that a primer extension or ligation event can be used as the indicator of a match or a mismatch. Hybridization with radioactively labeled ASOs has also been applied to the detection of specific SNPs (Connor, B. J. et al. (1983), Proc Natl Acad Sci USA, 80, 278-282). The method is based on the differences in the melting temperatures of short DNA fragments differing by a single nucleotide. Stringent hybridization and washing conditions can differentiate between mutant and wild-type alleles.

Denaturing/Temperature Gradient Gel Electrophoresis (DGGE/TGGE)—Two other methods rely on detecting changes in electrophoretic mobility in response to minor sequence changes. One of these methods, termed "Denaturing Gradient Gel Electrophoresis" (DGGE), is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can be used to detect the presence of SNPs in the target sequences due to the corresponding change in electrophoretic mobilities. The fragments to be analyzed, usually PCR products, are "clamped" at one end by a long stretch of G-C base pairs (30-80) to allow complete denaturation of the sequence of interest without complete dissociation of the strands. The attachment of a GC "clamp" to the DNA fragments increases the fraction of mutations that can be recognized by DGGE (Abrams, E. S. et al. (1990). Comprehensive detection of single base changes in human genomic DNA using denaturing gradient gel electrophoresis and a GC clamp. Genomics 7, 463-475). Attaching a GC clamp to one primer is critical to ensure that the amplified sequence has a low dissociation temperature (Sheffield, V. C. et al. (1989). Attachment of a 40-Base-Pair G+C-Rich Sequence (GC-Clamp) to Genomic DNA Fragments by the Polymerase Chain Reaction Results in Improved Detection of Single-Base Changes. Proc Natl Acad Sci 86, 232-236; and Lerman, L. S, and Silverstein, K. (1987). Computational simulation of DNA melting and its application to denaturing gradient gel electrophoresis. Meth Enzymol 155, 482-501). Modifications of the technique have been developed using temperature gradients (Wartell, R. M. et al. (1990). Detecting base pair substitutions in DNA fragments by temperature-gradient gel electrophoresis. Nucl Acids Res, 18(9), 2699-2705) and the method can be also applied to RNA:RNA duplexes (Smith, F. I. et al. (1988). Novel method of detecting single base substitutions in RNA molecules by differential melting behavior in solution. Genomics 3(3), 217-223).

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration. In addition, long running times are required for DGGE. The long running time of DGGE was shortened in a modification of the method called "Constant Denaturant Gel Electrophoresis" (CDGE) (Borresen, A. et al. (1991). Constant Denaturant Gel Electrophoresis as a Rapid Screening Technique for p53 Mutations. Proc Natl Acad Sci USA 88(19), 8405-8409). CDGE requires that gels be run under different denaturant conditions in order to reach high efficiency for the detection of SNPs.

A technique analogueous to DGGE, termed "Temperature Gradient Gel Electrophoresis" (TGGE), uses a thermal gradient rather than a chemical denaturant gradient (Scholz, R. B. et al. (1993). Rapid screening for Tp53 mutations by temperature gradient gel electrophoresis: a comparison with SSCP analysis. Hum Mol Genet. 2(12), 2155-2158). TGGE requires the use of specialized equipment that can generate a temperature gradient perpendicularly oriented relative to the electrical field. TGGE can detect mutations in relatively small fragments of DNA; therefore, scanning large gene segments requires the use of multiple PCR products prior to running the gel.

Single-Strand Conformation Polymorphism (SSCP)—Another common method, called "Single-Strand Conformation Polymorphism" (SSCP), was developed by Hayashi, Sekya, and colleagues (reviewed by Hayashi, K (1991). PCR-SSCP: A simple and sensitive method for detection of mutations in the genomic DNA. PCR Meth Appl 1, 34-38), and is based on the observation that single-strand nucleic acids can take on characteristic conformations under non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, M. et al. (1989a). Rapid and sensitive detection of point mutations and DNA polymorphisms using the polymerase chain reaction. Genomics 5, 874-879; Orita, M. et al. (1989b). Detection of Polymorphisms of Human DNA by Gel Electrophoresis as Single-Strand Conformation Polymorphisms. Proc Natl Acad Sci USA 86, 2766-2770).

The SSCP process involves denaturing a DNA segment (e.g., a PCR product) that is labeled on both strands, followed by slow electrophoretic separation in a non-denaturing polyacrylamide gel to allow intra-molecular interactions to form without disturbance during the run. This technique is extremely sensitive to variations in gel composition and temperature. A serious limitation of this method is the relative difficulty encountered in comparing data generated in different laboratories, under apparently similar conditions.

Dideoxy fingerprinting (ddF)— Dideoxy fingerprinting (ddF) is another technique developed to scan genes for the presence of mutations (Liu, Q. and Sommer, S. S. (1994). Parameters affecting the sensitivities of dideoxy fingerprinting and SSCP. PCR Methods Appl 4, 97-108). The ddF technique combines components of Sanger dideoxy sequencing with SSCP. First, a dideoxy sequencing reaction is performed using one dideoxy terminator. Next, the reaction products are electrophoresed on non-denaturing polyacrylamide gels to detect alterations in mobility of the termination segments, as in SSCP analysis. While ddF is an improvement over SSCP in terms of increased sensitivity, ddF requires the use of expensive dideoxynucleotides and the technique is still limited to the analysis of fragments of the size suitable for SSCP (i.e., fragments of 200-300 bases) for optimal detection of mutations.

In addition to the above limitations, all of these methods for detecting single mutations are limited as to the size of the nucleic acid fragment that can be analyzed. For the direct sequencing approach, sequences of greater than 600 base pairs require cloning, with the consequent delays and expense of either deletion sub-cloning or primer walking, in order to cover the entire fragment. SSCP and DGGE have especially severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base-pair fragments. Similarly, the sensitivity of DGGE decreases as the length of the fragment reaches 500 base pairs. The ddF technique, as a combination of direct sequencing and SSCP, is also limited by the relatively small size of the DNA that can be screened.

Pyrosequencing™ analysis—This technique (Pyrosequencing, Inc., Westborough, Mass., USA) is based on the hybridization of a sequencing primer to a single-stranded, PCR-amplified DNA template in the presence of DNA polymerase, ATP sulfurylase, luciferase, and apyrase enzymes and the adenosine 5'-phosphosulfate (APS) and luciferin substrates. In the second step the first of four deoxynucleotide triphosphates (dNTP) is added to the reaction and the DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. In the last step the ATP sulfurylase quantitatively converts PPi to ATP in the presence of adenosine 5'-phosphosulfate. The ATP drives the luciferase-mediated conversion of luciferin to oxyluciferin that generates visible light in amounts that are proportional to the amount of ATP. The light produced in the luciferase-catalyzed reaction is detected by a charge-coupled device (CCD) camera and seen as a peak in a Pyrogram™. The strength of each light signal is proportional to the number of nucleotides incorporated.

Acycloprime™ analysis—This technique (PerkinElmer, Boston, Mass., USA) is based on fluorescent polarization (FP) detection. Following PCR amplification of the sequence containing the SNP of interest, excess primer and dNTPs are removed through incubation with shrimp alkaline phosphatase (SAP) and exonuclease I. Once the enzymes are heat-inactivated, the Acycloprime-FP process uses a thermostable polymerase to add one of two fluorescent terminators to a primer that ends immediately upstream of the SNP site. The terminator(s) added are identified by their increased FP and represent the allele(s) present in the original DNA sample. The Acycloprime process uses AcycloPol™, a novel mutant thermostable polymerase from the domain Archaea, and a pair of AcycloTerminators™ labeled with R110 and TAMRA, representing the possible alleles for the SNP of interest. AcycloTerminator non-nucleotide analogues are biologically active with a variety of DNA polymerases. Similarly to 2',3'-dideoxynucleotide-5'-triphosphates, the acyclic analogues function as chain terminators. The analogue is incorporated by the DNA polymerase in a base-specific manner onto the 3'-end of the DNA chain; since there is no 3'-hydroxyl, the polymerase is unable to function in further chain elongation. It has been found that AcycloPol has a higher affinity and specificity for derivatized AcycloTerminators than various Taq mutants have for derivatized 2',3'-dideoxynucleotide terminators.

Reverse dot-blot—This technique uses labeled sequence-specific oligonucleotide probes and unlabeled nucleic acid samples. Activated primary amine-conjugated oligonucleotides are covalently attached to carboxylated nylon membranes. After hybridization and washing, the labeled probe or a labeled fragment of the probe can be released using oligomer restriction, i.e., the digestion of the duplex hybrid with a restriction enzyme. Circular spots or lines are visualized colorimetrically after incubation with streptavidin horseradish peroxidase, followed by development using tetramethylbenzidine and hydrogen peroxide, or alternatively via chemiluminescence after incubation with avidin alkaline phosphatase conjugate and a luminous substrate susceptible to enzyme activation, such as CSPD, followed by exposure to x-ray film.

It will be appreciated that advances in the field of SNP detection have provided additional accurate, easy, and inexpensive large-scale SNP genotyping techniques, such as: dynamic allele-specific hybridization (DASH) (Howell, W. M. et al. (1999). Dynamic allele-specific hybridization (DASH). Nat Biotechnol 17, 87-88); microplate array diagonal gel electrophoresis (MADGE) (Day, I. N. et al. (1995). High-throughput genotyping using horizontal polyacrylamide gels with wells arranged for microplate array diagonal gel electrophoresis (MADGE). Biotechniques 19, 830-835); the TaqMan® system (Holland, P. M. et al. (1991). Detection of specific polymerase chain reaction product by utilizing the 5'→3' exonuclease activity of *Thermus aquaticus* DNA polymerase. Proc Natl Acad Sci USA 88, 7276-7280); various DNA "chip" technologies such as GeneChip® microarrays (e.g., SNP chips, Affymetrix, USA), which is disclosed in U.S. Pat. No. 6,300,063 to Lipshutz et al. 2001, which is fully incorporated herein by reference; genetic bit analysis (GBA®), described by Goelet, P. et al. (PCT Appl. No. 92/15712); peptide nucleic acids (PNA) (Ren, B. et al. (2004). Straightforward detection of SNPs in double-stranded DNA by using exonuclease III/nuclease S1/PNA system. Nucleic Acids Res. 32(4), e42) and locked nucleic acid (LNA) probes (Latorra, D. et al. (2003). Enhanced allele-specific PCR discrimination in SNP genotyping using 3' locked nucleic acid (LNA) primers. Hum Mutat 22(1), 79-85); molecular beacons (Abravaya, K. et al. (2003). Molecular beacons as diagnostic tools: technology and applications. Clin Chem Lab Med 41, 468-474); intercolating dyes (Germer, S, and Higuchi, R. (1999). Single-tube genotyping without oligonucleotide probes. Genome Res 9, 72-78); FRET primers (Solinas, A. et al. (2001). Duplex Scorpion primers in SNP analysis and FRET applications. Nucleic Acids Res 29(20), E96); AlphaScreen™ (Beaudet, L. et al. (2001). Homogeneous assays for single-nucleotide polymorphism typing using AlphaScreen. Genome Res 11(4), 600-608); SNPstream® (Bell, P. A. et al. (2002). SNPstream UHT: ultra-high throughput SNP genotyping for pharmacogenomics and drug discovery. Biotechniques Supplement 70-72, 74, 76-77); multiplex minisequencing (Curcio, M. et al. (2002). Multiplex high-throughput solid-phase minisequencing by capillary electrophoresis and liquid core waveguide fluorescence detection. Electrophoresis 23(10), 1467-1472); SnaPshot™ Multiplex System (Turner, D. et al. (2002). Typing of multiple single nucleotide polymorphisms in cytokine and receptor genes using SNaPshot. Hum Immunol 63(6), 508-513); MassEXTENDT™ (Cashman, J. R. et al. (2001). Population distribution of human flavin-containing monooxygenase form 3: gene polymorphisms. Drug Metab Dispos 29, 1629-1637); GOOD assay (Sauer, S, and Gut, I. G. (2003). Extension of the GOOD assay for genotyping single nucleotide polymorphisms by matrix-assisted laser desorption/ionization mass spectrometry. Rapid Commun Mass Spectrom 17, 1265-1272); microarray minisequencing (Liljedahl, U. et al. (2003). A microarray minisequencing system for pharmacogenetic profiling of antihypertensive drug response. Pharmacogenetics 13, 7-17); arrayed primer extension (APEX) (Tonisson, N. et al. (2000). Unravelling genetic data by arrayed primer extension. Clin Chem Lab Med 38, 165-170); microarray primer extension (O'Meara, D. et al. (2002). SNP typing by apyrase-mediated allele-specific primer extension on DNA microarrays. Nucleic Acids Res 30, e75); tag arrays (Fan, J. B. et al. (2000). Parallel genotyping of human SNPs using generic high-density oligonucleotide tag arrays. Genome Res 10(6), 853-860); template-directed incorporation (TDI) (Akula, N. et al. (2002). Utility and accuracy of template-directed dye-terminator incorporation with fluorescence-polarization detection for genotyping single nucleotide polymorphisms. Biotechniques 32, 1072-1076, 1078); fluorescence polarization (Hsu, T. M. et al. (2001). Universal SNP genotyping assay with fluorescence polarization detection. Biotechniques 31, 560, 562, 564-568, passim); colorimetric oligonucleotide ligation assay (OLA) (Nickerson, D. A. et al. (1990). Automated DNA diagnostics using an ELISA-based oligonucleotide ligation assay. Proc Natl Acad Sci USA 87, 8923-8927); sequence-coded OLA (Gasparini, P. et al. (1999). Analysis of 31 CFTR mutations by polymerase chain reaction/oligonucleotide ligation assay in a pilot screening of 4476 newborns for cystic fibrosis. J Med Screen 6, 67-69); microarray ligation; ligase chain reaction; padlock probes; rolling circle amplification; invader assays (Shi, M. M. (2001). Enabling large-scale pharmacogenetic studies by high-throughput mutation detection and genotyping technologies. Clin Chem 47, 164-172); coded microspheres (Rao, K. V. et al. (2003). Genotyping single nucleotide polymorphisms directly from genomic DNA by invasive cleavage reaction on microspheres. Nucleic Acids Res 31, e66); MassARRAY™ (Leushner, J. and Chiu, N. H. (2000). Automated mass spectrometry: a revolutionary technology for clinical diagnostics. Mol Diagn 5, 341-348); heteroduplex analysis; mismatch cleavage detection; exonuclease-resistant nucleotide derivative (U.S. Pat. No. 4,656,127); and other conventional techniques as described in: Sheffield et al. (1989); White, M. B. et al. (1992). Detecting single base substitution as heteroduplex polymorphisms. Genomics 12, 301-306; Grompe, M. et al. (1989). Scanning detection of mutations in human ornithine transcarbamoylase by chemical mismatch cleavage. Proc Natl Acad Sci USA 86(15), 5888-5892; and Grompe, M. (1993). The rapid detection of unknown mutations in nucleic acids. Nat Genet 5, 111-117.

As mentioned hereinabove, sequence alterations (e.g., the Val/Ala at position 57 of the CD24 polypeptide set forth in SEQ ID NO:2, the Ile/Lys at position 1307 of the APC polypeptide set forth in SEQ ID NO:8 and/or the Glu/Gln at position 1317 of the APC polypeptide set forth in SEQ ID NO:8) can also be determined at the protein level.

Briefly, proteins are extracted from a sample of any source of cells or cell content of the subject (as described hereinabove) and the presence of the specific polymorphs of the CD24 and APC proteins is detected. While chromatography and electrophoretic methods are preferably used to detect large variations in CD24 molecular weight, such as detection of a truncated CD24 or APC protein generated by the CD24 or APC sequence alterations, immunodetection assays such as ELISA and Western blot analysis, immunohistochemistry, and the like, which may be effected using antibodies specific to CD24 or APC sequence alterations, are preferably used to detect point mutations and subtle changes in molecular weight.

Thus, the present invention also envisages the use of serum immunoglobulins, polyclonal antibodies or fragments thereof (i.e., immunoreactive derivatives thereof), monoclonal antibodies or fragments thereof having at least a portion of an antigen-binding region, including the fragments described hereinbelow, chimeric or humanized antibodies, and complementarity-determining regions (CDR) for detection of sequence alterations in the protein level (e.g., the Val/Ala polymorphisms at position 57 of the CD24 polypeptide set forth by SEQ ID NO:2; and/or the Ile/Lys at position 1307 of the APC polypeptide set forth in SEQ ID NO:8; and/or the Glu/Gln at position 1317 of the APC polypeptide set forth in SEQ ID NO:8).

The reagents described hereinabove for detection of immunocomplex formation (e.g., for determining CD24 presence and/or level in a biological sample) or hybridization when oligonucleotides are used [e.g., for determining the of a specific CD24 (e.g., the thymidine nucleotide at position 280 of SEQ ID No:1) or APC (e.g., the adenosine nucleotide at position 3977 of SEQ ID NO:7 and/or the cytosine nucleotide at position 4006 of SEQ ID NO:7) genotype of a subject] may be included in a diagnostic kit/article of manufacture preferably along with appropriate instructions for use and labels indicating FDA approval for use in diagnosing cancer or a pre-malignant lesion, for monitoring efficacy of cancer therapy and/or for determining the predisposition of a subject to gastrointestinal cancer.

Such a kit can include, for example, at least one container including at least one of the above described diagnostic agents (e.g., a CD24 specific antibody, a CD24 oligonucleotide capable of hybridizing a specific CD24 polymorph) and an imaging reagent packed in another container (e.g., enzymes, secondary antibodies, buffers, chromogenic substrates, fluorogenic material). The kit may also include appropriate buffers and preservatives for improving the shelf-life of the kit.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

CD24 Expression is Regulated in Ras Mutant Transformed Cell Lines

Differential gene expression analysis, using microarrays, provides a comprehensive profile of the relative mRNA levels, thus providing new insight into the various biologic pathways involved in disease pathogenesis, progression, and response to therapy. This technique emerges as a valuable potential tool for classifying histologically similar tumors into molecularly specific subtypes, which may predict clinical outcome in individual patients. Microarray technology has been applied successfully in the study of many malignancies, including CRC (12-16).

To identify genes involved in CRC progression, the present inventors have transfected normal enterocytes with a variety of oncogenes and evaluated the gene expression pattern of the transformed cells before and after the exposure to Celecoxib (Pfizer, NY, USA), a specific COX-2 inhibitor, using the rat Affymetrix expression array, as follows.

Materials and Experimental Methods

In vitro cell model—The present inventors have developed an in vitro model which consisted of a variety of normal and transformed intestinal cell lines. Normal enterocytes derived from rat ileum (IEC 18 cells), were transfected with a variety of oncogenes. Among them, mutant ras transformed enterocytes (designated R1 cells) posses a very aggressive phenotype. These cells were produced by co-transfection of the drug resistance selectable marker tk-neo and the plasmid pMIKcys, which encodes a mini human c-K-ras gene (15 kb) that contains a cysteine mutation at codon 12. Ras mutations are found in the majority of CRC patients. This cell line-based system is much more coherent and useful when one wishes to apply the new technique of expression micro-array, because it consists only of normal and malignant cells and is devoid of inflammatory, necrotic and stromal cells that might obstruct and mask the true effect of the malignant transformation.

Gene expression studies were performed using the Affymetrix rat (RG-U34) Genechip® according to manufacturer's instructions using RNA from the in vitro cell model.

Experimental Results

CD24 is upregulated in intestinal cells transformed with Ras mutants and its expression level is reversed following treatment with Celecoxib—To characterize altered gene expression pattern following malignant transformation in intestinal epithelial cells, RNA extracted from intestinal cell lines transformed with various oncogenes was subjected to analysis using the rat expression arrays [Affymetrix rat (RG-U34) Genechip®]. Specifically, differential gene expression was analyzed to compare IEC-18 and R1 cells [Sutter T, Miyake M, Kahn S M, Venkatraj V S, Sobrino A, Warburton D, Holt P R, Weinstein I B. Increased expression of cyclin D1 and the Rb tumor suppressor gene in c-K-ras transformed rat enterocytes. Oncogene 2; 12(9):1903-8, 1996], before and after short and long durations of exposures to Celecoxib (Pfizer, NY, USA), a specific COX-2 inhibitor and a proved chemo-preventive agent in the colon. Scanned output files were analyzed and the expression value of each gene was determined. Of the approximately 20,000 genes present on the Affymetrix chip, 1,081 were differentially expressed (>2-fold) in tumor cells (Sagiv E., et al., 2006, Gastroenterology, 131: 630-639; and data not shown). Of these, a cluster of 71 genes showed a reversion to normal expression levels following short and long treatments with celecoxib. One of the genes showing reversal to normal expression is the gene encoding for CD24 (GenBank Accession No. NM_013230; SEQ ID NO:1).

Example 2

CD24 is Overexpressed at Early Events of CRC Carcinogenesis

As described in the Background section hereinabove, Weichert W., et al. (Clin. Cancer Res. 2005, 11: 6574-6581) tested the expression pattern of CD24 in 146 colorectal carcinomas (CRC) and found that while in 68.7% of the tumors CD24 exhibited a membranous staining, in 84.4% of the tumors CD24 is expressed in the cytoplasm. In addition, in 10% of the cases an exceptionally strong cytoplasmic CD24 expression was observed which correlated with higher tumor stage and poorer prognosis. However, to date the expression level of CD24 in pre-malignant tumors of the GI tract was never tested.

Based on the regulated expression pattern of CD24 in cell lines transformed with ras mutants (see Example 1, hereinabove), and in order to determine the involvement of CD24 in the early events leading to GI tracts carcinogenesis, immunohistochemical analyses were performed in a comprehensive group of 398 samples including normal tissue, pre-malignant tumors and malignant tumors of the entire GI tract, as follows.

Materials and Experimental Methods

Immunohistochemical analysis—Immunohistochemical analyses were performed with an avidin-biotin complex immunoperoxidase technique (Umansky M., Rattan J., et al., Oncogene 2001; 20: 7987-7991). Four-micrometer tissue sections were mounted on poly-L-lysine-coated slides. After deparaffinization in Americlear (Baxter, McGaw Parl, IL) and absolute ethanol, sections were hydrated through a series of graded alcohol, distilled water, and phosphate-buffered saline (PBS) at pH 7.4. Slides were then immersed in 10 mM citrate buffer (pH 6) and microwaved at 750 W for a total of 10 minutes. After blocking with goat serum for 20 minutes, the primary antibodies, anti CD24 monoclonal antibody (Ab-2, clone 24Co2; Neo-markers, Fremont, CA), were applied and incubated overnight at 4° C. in a high-humidity chamber. Although all concentrations of primary antibody gave good membranous staining, the ideal concentration with minimal background was 20 µg/ml. As a negative control, duplicate sections of selected tissue samples were immunostained in the absence of the primary antibody. Subsequent steps utilized the Vectastain rabbit Elite ABC kit (Vector Laboratories, Burlingame, CA) according to the manufacturer's instructions. Color development was accomplished with 0.375 mg/dL of 3,3'-diaminobenzidine tetrahydrochloride solution (Sigman Chemical, Co, St. Louis, MO) containing 0.0003% hydrogen peroxide. Slides were counterstained with hematoxylin and dehydrated, and coverslips were applied using Acrytol mounting medium (Surgipath Medical Industries, Richmond, Il).

Experimental Results

CD24 is over-expressed in various adenomas and carcinomas of the colon, rectum and entire GI tract—As is shown in Table 1, hereinbelow, the immunohistochemical analysis validated the array results related to the over-expression of this gene (CD24) in respect to the cellular protein milieu, as well as the projection of the results obtained from the rat model onto human CRC tissues. To this end, CD24 expression was determined in 398 samples spanning the entire GI tract (benign and malignant), 66 of them were CRC samples.

Positive luminal membrane staining for CD24 was seen in 49 out of 54 (90.7%) colorectal adenomatous polyps (pre-malignant tumors) and in 57 out of 66 (86.3%) adenocarcinomas (Table 1). It should be noted that the positive membrane staining was to the same extent in the pre-malignant (adenomas) as in the malignant tumors. On the other hand, membrane staining was positive in only 9 out of 54 (16.6%) normal appearing mucosa, adjacent to CRC samples. Positive membrane staining was not related to the gender or age of the patient, neither to the size or degree of dysplasia in adenomatous polyps (data not shown). In addition, positive membrane staining was seen in 77.9% of the pre-malignant adenomas of the entire GI tract and in 71.2% of the carcinomas of the entire GI tract (Table 1).

TABLE 1

Immunohistochemical analysis of CD24 in CRC and other GI tumors

| CD24 staining | Colon and Rectum | | | Entire GI tract | | |
|---|---|---|---|---|---|---|
| | Normal Tissue | Adenoma | Carcinoma | Normal Tissue | Adenoma | Carcinoma |
| Negative N (%) | 45 (83.3) | 5 (9.2) | 9 (13.6) | 122 (83) | 21 (22.1) | 45 (28.8) |
| Positive N (%) | 9 (16.6) | 49 (90.7) | 57 (86.3) | 25 (17) | 74 (77.9) | 111 (71.2) |
| Total N (%) | 54 (100) | 54 (100) | 66 (100) | 147 (100) | 95 (100) | 156 (100) |

Table 1: 398 normal and tumor specimens obtained from normal adjacent mucosa and tumors of the entire GI tract (esophagus, stomach, pancreas, small and large bowel) were stained for CD24 using monoclonal anti-CD24 antibodies (Ab-2, clone 24C02; Neomarkers, Fremont, CA) and the staining of the membrane was recorded according to an intensity score on a scale of 0, 1, 2, and 3 of increasing intensity. Shown are the frequencies of positive membrane staining (of an intensity score higher than "1") in normal tissue, adenomas (pre-malignant lesions) and carcinomas of the entire GI tract (including the colon and rectum) as well as in the colon and rectum as a separate group.

The fact that CD24 was expressed to the same extent in adenomas (the pre-malignant stage of a carcinoma) as well as in all stages of CRC or the entire GI tract carcinomas indicates that expression of CD24 is an early event in the multi-step process of CRC carcinogenesis. Thus, the expression of CD24, not only in carcinomas (CRC and the entire GI tract), but already at the pre-malignant lesion, e.g., adenomatous polyp suggests the use of CD24 as an early marker carcinogenic processes of the entire GI tract.

Example 3

Polymorphism in the CD24 Gene is of a Clinical Significance

Very little is known about polymorphism in the CD24 gene. Zhou Q., et al. 2003 (Proc. Natl. Acad. Sci. 100: 15041-15046) have described a single nucleotide polymorphism (SNP) in the human CD24 gene (C→T substitution at position 280 of GenBank Accession No. NM_013230; SEQ ID NO:1) resulting in a missense mutation [GCG (Ala)→GTG (Val) at position 57 of the CD24 protein set forth by SEQ ID NO:2; GenBank Accession No. NP_037362) immediately after the putative cleavage site of the GPI anchor, that is associated with an increased risk and a more rapid progression of Multiple Sclerosis.

The APC gene [protein—GenBank Accession No. NP_000029.2 (SEQ ID NO:8), mRNA—GenBank Accession No. NM_000038.3 (SEQ ID NO:7)] encodes a tumor suppressor protein, and is widely mutated as a first event in the carcinogenesis process of the colon and rectum. Laken et al (Laken S J, Petersen G M, Gruber S B, Oddoux, Vogelstein B. Familial colorectal cancer in Ashkenazim due to a hypermutable tract in APC. Nat Genet. 17: 79-83, 1997) identified the I1307K which results in a substitution of Lysine (K) for Isoleucine (I) in codon 1307 of the protein. The change does not affect the functionality of the protein but creates a sequence of 8 Adenines in the genes, which increase the risk for mistakes in the DNA polymerase activity and thus a 500 bp region in high risk for mutability (Laken SJ, et al., 1997). Previous studies performed by the present inventors (H. Strul, et al., 2003) demonstrated that this polymorphism does not contribute to the assessment of the risk for CRC.

E1317Q polymorphism in the APC protein does not have a known functional or phenotypic effect but it causes a mismatch repair activity and is related to higher risk for colorectal neoplasia.

Materials and Experimental Methods

Genotyping—Genomic DNA was extracted from peripheral blood lymphocytes. About 200 ng DNA were taken for real-time PCR reaction (for the APC SNPs) or RFLP analysis (for the CD24 SNP), as follows.

Determination of the Ala/Val polymorphism at position 57 of the CD24 protein—Genomic DNA was PCR amplified using the following primers: Forward: 5'-TTGTTGCCACT-TGGCATTTTTGAGGC (SEQ ID NO:3) and Reverse: 5'-GGATTGGGTTTAGAAGATGGGGAAA (SEQ ID NO:4) at annealing temperature of 50° C. The resulting CD24 PCR product is of 520 bp. The C→T change at position 280 of SEQ ID NO:1 yields a BstXI restriction enzyme site at nucleotide 327 of the PCR product, which allows the differentiation of the two CD24 alleles by restriction fragment length analysis. Thus, the DNA encoding the Val-57 polymorph is digested by BstXI to about 320 and 200 by and the DNA encoding the Ala-57 polymorph is undigested by BstXI and thus is of 520 bp.

Determining the I1307K polymorphism in the APC gene—The I1307K polymorphism is a substitution of isoleucine (I) (common allele) with lysine (K) (rare allele) at position 1307 of GenBank Accession No. NP_000029.2; SEQ ID NO:8; which results from the T→A substitution at nucleotide 3977 of NM_000038.3; SEQ ID NO:7. Briefly, genomic DNA was PCR amplified using the following primers: Forward 5'-GAT-TCTGCTAATACCCTGCAAATAGCA-3' (SEQ ID NO:5) and reverse 5'-CCCTGCAGTCTGCTGGATTTGG-3' (SEQ ID NO:6) primers. For real time PCR a sensor primer is designed according to the wild-type allele and downstream to it an anchor primer. Light reaction changes according to the temperature in which the sensor binds to the DNA and meets the anchor; the temperature is elevated with time and the time of reaction is measured. For the detection of the specific polymorphic nucleotide (T/A at position 3977 of SEQ ID NO:7) the anchor primer was: LC-Red640-TTTGCAGGG-TATTAGCAGAATCTGCTTCCTGTG-ph (SEQ ID NO:9) and sensor primer was: CCAATCTTTTCTTTTTTTTCT-FL (SEQ ID NO:10).

Determination of the E1317Q polymorphism in the APC gene—The E 1317Q polymorphism is a substitution of Glutamic acid (E) (common allele) with Glutamine (Q) (rare allele) at position 1317 of GenBank Accession No. NP_000029.2; SEQ ID NO:8; which results from the G→C substitution at nucleotide 4006 of NM_000038.3; SEQ ID NO:7. Briefly, genomic DNA was PCR amplified using the following primers: Forward 5'-GATTCTGCTAATACCCTG-CAAATAGCA-3' (SEQ ID NO:5) and reverse 5'-CCCTG-CAGTCTGCTGGATTTGG-3' (SEQ ID NO:6) primers and detection of the specific polymorphic nucleotide (G/C at position 4006 of SQ ID NO:7) was by real time PCR using the anchor primer: TGCTGTGACACTGCTGGAACTTCGC-FL (SEQ ID NO:11) and sensor primer: ph-LC-Red705-CA-CAGGATCTTGAGCTGACCTAG (SEQ ID NO:12).

Experimental Results

CD24 expression is depended on the CD24 genotype at position 57 (Ala/Val 57)—Using the CD24 RFLP test the present inventors have found that HT29 cells, that express high level of the CD24 protein, exhibit the CD24$^{v/v}$ (Val/Val at position 57 of the CD24 protein) genotype whereas, Panc1 cells and HCT116 cells that barely express the protein carry the CD24$^{a/a}$ (Ala/Ala at position 57 of the CD24 protein) genotype. These results suggest that over-expression of the CD24 protein is associated with the Val-57 polymorph of CD24 protein. Still the majority of CD24 bearing CRC will not have the a/a genotype. In order to confirm this hypothesis, the CD24 genotypes were analyzed from peripheral blood DNA and the frequencies of the three genotypes were determined.

FIG. 4 depicts an example of the genotype analysis performed using restriction fragment length polymorphism (RFLP) of the Ala57Val polymorphism of the CD24 gene using the BstXI restriction enzyme.

The Val-57 polymorph is associated with increased risk to CRC carcinogenesis—A dataset of 1064 individuals (normal healthy subjects and CRC patients) with mean age 58.68 years, std. dev: 14.78, revealed that 61.75% of the population were Israeli Ashkenazi Jews and 25.47% were Israeli Sephardic Jews (the rest are mixed or other ethnic groups). Among the tested population, Sephardic Jews showed a significant association for harboring the common A/A (Ala) genotype: OR 1.3 [1.0-1.8]p=0.04. It should be noted, that the prevalence of CRC in Sephardic Jews is smaller than in Ashkenazi Jews (Darwish H, Trejo I E, et al., 2002. Fighting colorectal cancer: molecular epidemiology differences among Ashkenazi and Sephardic Jews and Palestinians. Ann Oncol., 13: 1497-501; Rozen P, Lynch H T, Figer A et al. Israel Cancer Registry, Cancer in Israel, Ministry of Health, Jerusalem, 1987. Familial colon cancer in the Tel-Aviv area and the influence of ethnic origin. Cancer; 60:2355-2362). Thus, these results suggest that the Ala polymorph at position 57 of the CD24 protein, especially in its homozygous state, is a protective genotype against CRC, and on the other hand, the Val-57 polymorph of the CD24 protein is a risk genotype for CRC.

As is further shown in Tables 2 and 3, hereinbelow, screening of 890 subjects of them 393 were diagnosed with CRC and 498 were healthy subjects revealed that the Val/Val genotype (Table 2) and the Val allele (Table 3) is more prevalence in CRC affected subjects that in healthy controls, thus suggesting association of the Val-57 polymorph with CRC.

TABLE 2

Genotype frequencies of the CD24 Ala/Val 57 polymorphism

| Genotypes | Total subjects | VV | AV | AA |
|---|---|---|---|---|
| CRC | 392 | 31 (7.9%) | 144 (36.7%) | 217 (55.35%) |
| Normal | 498 | 34 (6.8%) | 176 (35.35%) | 288 (57.83%) |

TABLE 3

Allele frequencies of the CD24 Ala/Val 58 polymorphism

| | Total Chromosomes | Val allele | Ala allele |
|---|---|---|---|
| CRC | 784 | 206 (26.275%) | 578 (73.72%) |
| Normal | 996 | 244 (24.49%) | 752 (75.50%) |

Combined genotypes in CD24 and APC genes are highly associated with increased risk to colorectal neoplasia or cancee—To further test the association of combined genotypes in the CD24 and APC genes, 375 subjects with A/V genotype (at position 57) of the CD24 protein were tested for the presence of the E1317Q polymorphism in the APC protein. 7 out of 375 subjects were positive for the E1317Q polymorphism (i.e., exhibited one allele of the 1317Q polymorph in the APC protein). Six out of the seven (85.7%) subjects which were CD24 A/V and APC E1317Q had colorectal neoplasia. On the other hand, 368 subjects were negative for the 1317Q polymorph in the APC protein (i.e., exhibited only E1317). 162 out of the 368 subjects (44%) had colorectal neoplasia which yields an odds ratio (OR) of 7.62963 (Chi-square=4.83, p-value 0.028). Thus, these results demonstrate that among individuals who carry a mutation in the carcinogenesis initiating gene such as the APC E1317Q, the presence of a Val-57 polymorph of the CD24 protein is indicative of increased predisposition risk for colorectal cancer.

405 subjects with the A/V genotype (at position 57) of the CD24 protein were tested for the presence of the I1307K polymorphism in the APC protein. 31 out of 405 subjects were positive (i.e., exhibited at least one allele of the 1307K polymorph in the APC protein). 21 out of the 31 (67.7%) subjects which were CD24 A/V and APC I1307K had colorectal neoplasia. On the other hand, of the 374 subjects which were negative for the I1307K polymorphism in the APC protein (i.e., exhibited only the I1307 polymorph in the APC protein) 175 (46%) had neoplasia which results in OR of 2.388 (Chi-square 5.03; p-value=0.0249). Thus, these results demonstrate that among individuals who carry a mutation in the carcinogenesis initiating gene such as the APC I1307K, the presence of a Val-57 polymorph in the CD24 protein is indicative of increased predisposition risk for colorectal cancer.

Example 4

CD24 Detection in Stool, Serum or Urine as an Early Marker For GI Tract Malignancy As described in Example 2, hereinabove, CD24 was significantly over-expressed in pre-malignant tumors of the GI tract, such as colorectal adenomatous polyps and adenomatous polyps of the entire GI tract. These results suggest that CD24 expression may precede the conversion of the pre-malignant adenoma to a malignant adenocarcinoma. Given that CD24 is expressed on the cell surface and conjugated via a GPI anchor, the present inventors have hypothesized that CD24 which is shedded or found in membrane residues from cell blebbing or death may be detected in various biological samples derived from subjects having pre-malignant tumors, and its detection may serve as an early marker of GI tract carcinogenesis.

In order to determine the presence of CD24 in biological samples obtained using non-invasive methods (e.g., stool, urine and serum), the present inventors have set up experimental conditions for CD24 immunoprecipitation, as follows.

Materials and Experimental Methods

Immunoprecipitation (IP) analysis of serum (as well as stool or urine) samples—Serum samples (500 µl) were mixed with equal volumes (500 µl) of lysis buffer (40 mM Tris-HCl, pH 7.4, 4 mM EDTA, 2% NP40, 0.2% SDS) or phosphate buffered saline (PBS). Anti-mouse conjugated Sepharose beads (Sigma, Cat. No. A6531) (20 µl) were incubated for 1 hour with ±2-5 µg of the monoclonal anti-CD24 antibody (SWA11), and aliquots of the beads-antibody complex (20 µl) were then mixed with the lysed serum samples and incubated over-night in a cold-room while rotating. The resulting beads-immuno complexes which included the CD24 protein of the serum samples were collected (by short centrifugation) and washed 6 times with Hepes-saline buffer (20 mM HEPES, 150 mM NaCl, 0.1% Triton and 10% Glycerol), and then the CD24-immunoprecipitates were eluted by 4× protein sample buffer (200 mM Tris-HCl pH 6.8, 40% glycerol, 8% SDS, 0.2% Bromophenol blue, 100 mM DTT) at 90-95° C. (5 minutes) followed by short centrifugation to separate the beads from the CD24 protein and the anti-CD24 antibody. The eluates were then subjected to Western blot analysis using the SWA11 anti-CD24 antibody.

Alternatively, serum samples were incubated with lysis buffer or PBS (as described hereinabove) and immunoprecipitation was performed with beads conjugated to Concavalin A, which binds to glycosilated proteins. The beads-immunocomplexes were then separated from the sample (by short centrifugation), followed by elution at 90-95° C. The eluants (containing the CD24 protein) were then subjected to SDS-PAGE followed by Western blot analysis with the SWA11 CD24 antibody.

Western blot analysis—was performed on cell lysates prepared using the following lysis buffer: 20 mM Tris-HCl, pH 7.4, 2 mM EDTA, 1% NP40, 0.1% SDS, or in the presence of PBS using the SW11 antibody similarly to the Western blot performed following IP analysis. Briefly, the amount of protein in the cell extracts is determined (e.g., using the Bradford assay) and 16 µg of total protein is loaded in each well.

Experimental Results

Calibration of the CD24 IP assay—The CD24 antibodies ML5 and SWA11 (Jackson D, Waibel R, Weber E, Bell J, Stahel R A. CD24, a signal-transducing molecule expressed on human B cells, is a major surface antigen on small cell lung carcinomas. Cancer Res. 1992; 52:5264-7) were employed in order to calibrate the IP assay. Extracts of the HCT116 (which do not express CD24) or HT29 (which express CD24) CRC cell lines were subjected to CD24-IP (using the anti-mouse Sepharose beads) followed by Western blot analysis with either ML5 or SWA11 antibodies. As is shown in FIG. 1, the SWA11 antibody was found to be an efficient antibody for IP analysis, yielding low background.

Determination of the sensitivity of the CD24 IP analysis— In order to learn about the sensitivity of the method, lysates from HT29 cells, which express CD24, were homogenized with increasing concentrations of normal sera followed by IP analysis. The CD24 protein was visible when 1 mg, 100 µg and 10 µg lysates were mixed in 1 ml serum but not in 1 µg and less (data is not shown). The experiment was repeated twice, changing each time the incubation times of the beads-Ab complex with the samples in-order to increase sensitivity and reduce background signals.

Figure 5:
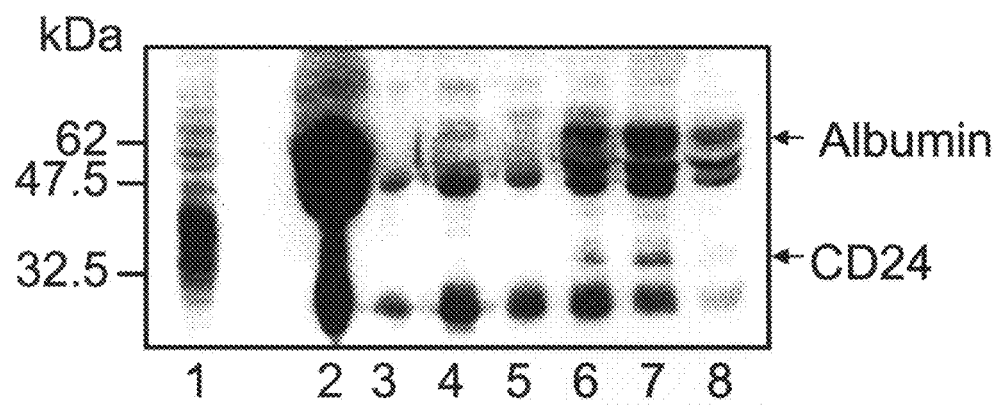
FIG. 5 depicts the purification of CD24 from human serum. CD24 in serum samples from patients with active CRC was purified by anion exchange chromatography using a DEAE-cellulose (DE52) minicolumn. Prior to fractionation, the serum was centrifuged at 12,000×g (30 minutes, 4° C.) in order to remove any remaining debris, and the albumin was depleted from serum using the DAC (Depletion of albumin component) protocol, which was modified from a previously published method [Colantonio D A, et al., 2005, Proteomics, 5(15): 3831-5]. Following albumin depletion, the serum was diluted in 10 mM Tris-HCl pH 7.4 and loaded on a DE52 minicolumn pre-equilibrated in the same buffer. The flow-through (FT) and wash (W) were collected separately and bound protein was eluted with increasing concentrations of NaCl (0.05-0.3 M) in Tris-HCl pH 7.4. Eluted proteins were analyzed by SDS-PAGE and Western blotting using the SWA11 monoclonal antibody. Lane 1—total lysate of HT29 cell lines serves as a positive control for the CD24 molecular weight; lane 2—a sample of the serum sample following the centrifugation but before albumin depletion; lanes 3-8—are different elution fractions. Note the presence of a protein with an apparent molecular weight of 35-40 kDa in lanes 6 and 7 that was eluted in fractions containing 0.1-0.2 M NaCl and recognized by the anti-CD24 antibody.

CD24 IP analysis in serum samples—In order to determine if the over-expression of CD24 in GI tumors (pre-malignant and malignant) is associated with the presence of CD24 in the serum, samples of serum from patients whose tumor biopsies were formerly positively stained by CD24 IHC were subjected to IP analysis using CD24 monoclonal antibodies or conconavalin A conjugated beads (conconavalin A binds glycosilated proteins). Briefly, serum samples (0.5 ml) were incubated over-night with precipitating beads which were prepared by pre-incubation of anti-mouse conjugated Sepharose beads (Sigma, Israel) with the SWA11 anti-CD24 monoclonal antibody. In patients whose sera were taken at time when CRC was active, a signal of a 35-40 kDa protein was observed, corresponding to the CD24 protein in patients. On the other hand, in patients whose sera was taken when CRC was non-active (in remission), there was either no expression or significantly reduced expression of CD24 (FIG. 3 and data not shown). CD24 was also purified from serum sample of a patient with active CRC by anion exchange chromatography using a DEAE-cellulose (DE52) minicolumn and albumin depletion, followed by Western blot analysis with the SWA11 monoclonal anti CD24 antibody (FIG. 5). These results demonstrate the presence of CD24 protein in serum of subjects with active CRC and suggest its detection in serum as a marker for GI malignancies.

CD24 Western blot analysis in stool and urine samples— Over 90 samples of stool and urine from CRC patients and healthy subjects, attendees at the Integrated Cancer Prevention Center (Sorasky Medical Center, Tel Aviv, Israel) were collected and stored at −80° C. All subjects signed informed consent under the approval of the hospital IRB and the ministry of health, and matching endoscopic reports were recorded. In order to analyze CD24 presence in stool samples, a small amount (0.3-0.5 ml) was snapped from the frozen sample and homogenized in 1 ml protein lysis buffer with protease inhibitors. Lysates were collected from the supernatant phase following centrifugation of the homogenate (20 minutes, 14,000 rpm). In 21/26 subjects who underwent colonoscopic examination and diagnosed with benign or malignant tumors CD24 was found in the stool (data not shown).

It should be noted that using either a lysis buffer (which removes membranal components) or PBS (which should not affect membranal components) there was no significant difference in the level of CD24 as detected by IP or Western blot analyses (data not shown) thus suggesting that the majority of CD24 detected in the serum was not membrane anchored.

The level of CD24 in the stool decreases following the removal of the tumor—In order to confirm that at least in part, the protein detected in the stool sample originates from the tumor, stool samples were collected from 11 patients before and after surgical/endoscopical removal of the tumor. Differences in the CD24 expression levels were visible among the paired samples (FIGS. 2*a-c*; and data not shown from a repeated experiment), demonstrating that the presence of CD24 in the stool originates at least in part from the tumors.

The level of CD24 in the stool decreases following radiation therapy—To further substantiate the relationship between CD24 in the stool and the presence of cancerous cells (active CRC disease) the level of CD24 was detected in CRC patients following the surgical removal of the tumor but before or after radiation therapy. As is shown in FIG. 2*b* (lanes 13 and 14), a significant decrease in the level of CD24 was noted after radiation therapy as compared to before treatment. Thus, these results demonstrate that the level of CD24 in the stool is in correlation with the presence of cancerous cells and can be used for monitoring efficacy of treatment.

Figure 2A:
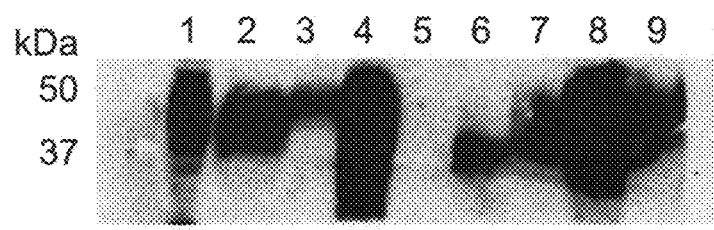
FIGS. 2a-c are CD24 Western blot analyses of stool samples obtained from CRC patients before and after the surgical removal of the tumor, or before and after chemotherapy treatment. Protein extracts (equal amounts) from stool samples of 12 patients (designated P-1, P-2, P-3 . . . P-12) diagnosed with colorectal tumors [adenomas or adenocarcinomas (CRC)] were subjected to Western blot analysis using the SWA11 Ab. The clinical manifestations of the patients before surgical removal are as following: patient 1 (P-1)—polyp 15 mm; patient 2 (P-2)—massive polyp; patient 3 (P-3)—polyp 20 mm; patient 4 (P-4)—polyp 5 mm, low grade dysplasia; patient 5 (P-5)—adenocarcinoma; patient 7 (P-7)—adenocarcinoma; patient 8 (P-8)—adenocarcinoma; patient 9 (P-9)—polyp 15 mm; patient 10 (P-10)—high grade polyp; patient 11 (P-11)—adenocarcinoma; patient 12 (P-12)—adenocarcinoma; patient 6 (P-6) carcinoma of the rectum—both his samples were taken after tumor removal but before (lane 13) or after (lane 14) radiation therapy.
Figure 2B:
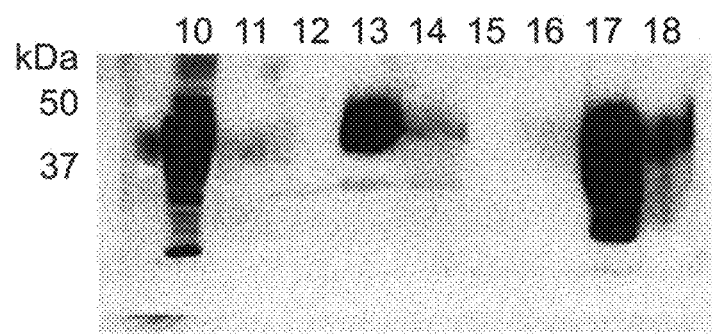
Figure 2C:
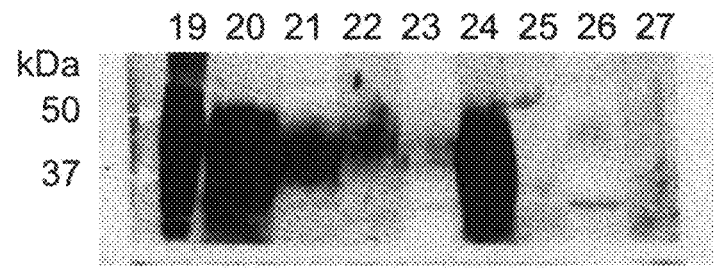
Figure 3:
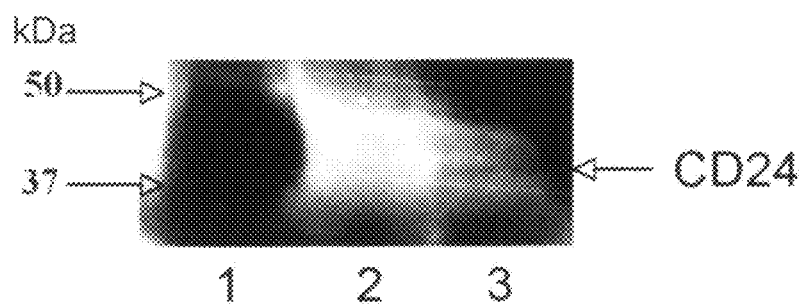
FIG. 3 depicts an immunoprecipitation analysis of CD24 in serum samples. Serum samples taken from patients having active CRC (lane 3) or non-active (lane 2) CRC were immunoprecipitated with a complex formed by pre-incubation of anti-mouse conjugated Sepharose beads (Sigma, Israel) with the SWA11 anti-CD24 monoclonal antibody. The immunoprecipitated complexes were subjected to Western blot analysis using the SWA11 anti-CD24 monoclonal antibody. Lane 1—HT29 cells over-expressing CD24; lane 2—serum from a patient having non-active CRC; lane 3—serum from a patient having active CRC. Note the ~40 kDa protein band in lane 3 and the absence of such protein band in lane 2, demonstrating the presence of CD24 in serum of subjects with active CRC and the disappearance of CD24 in subjects with non-active CRC.

The presence of low-molecular weight CD24 protein species is indicative of pre-cancerous or cancerous colon-rectal lesions—As seen in FIGS. 2*a-c*, in stool sample taken from patients before the surgical removal of the tumors or polyps there are various low molecular weight CD24-reactive bands of about 25-37 kDa which are absent from stool samples taken from the same patients after the surgical removal of the polyps or tumors. Without being bound to any theory, these results may indicate that the circulating CD24 which is present in stool, urine or serum samples of subjects having pre-malignant or malignant lesions comprises either only a portion of the CD24 amino acid sequence or represents a less glycosilated form (and therefore a lower molecular weight protein species) of CD24.

Altogether, these results demonstrate that detection of circulating CD24 in biological samples can be used as an early detection marker of cancer such as GI malignancies and/or for monitoring treatment efficacy of the cancer. In addition, the presence of low molecular weight species of CD24 (e.g., between 25 to 37 kDa) and/or high levels of CD24 (from any size from the range of 25-60 kDa) above a pre-determined threshold is indicative pre-malignant or malignant tumors.

Analysis and Discussion

The findings of the present study show that CD24 is expressed on the membrane of a distinctively high percentage of cells of pre-malignant and malignant tumors of the GI tract, including adenomas of the colon/rectum and of the rest of the alimentary tract (small intestine and upper GI tract). As a surface protein that is expressed at an early stage of tumor progression, while it rarely appears on normal tissues, the present inventors suggest CD24 as a novel highly reliable biomarker for cancer cells. In addition, the findings of CD24 in biological samples such as serum, stool and urine in subjects having pre-malignant or malignant lesions of the GI tract demonstrate, for the first time, that soluble, shedded or blebbed CD24 (circulating CD24) can be used in the diagnosis of pre-malignant and malignant lesions.

Given that CD24 is a short peptide, that is set on the outer side of the cells and has no transmembrane domain but only an anchor to GPI, it is likely to believe that a portion of the protein, which as is shown in-vitro, is produced excessively when is expressed, is constantly secreted from the tumor cells and reaches the bloodstream or cleaved by lipases at the extra-cellular matrix. Furthermore, necrotic tumor cells, their fragments or blebbing products of tumor cells, might reach the bloodstream as well and contain in them GPI anchored CD24 protein.

One of the anti-CD24 monoclonal antibodies, the SWA11, was found by the present inventors to efficiently detect CD24 in biological samples using either an IP analysis [together with the anti-Mouse conjugated beads (Sigma)] or as an immuno-blotting antibody (e.g., the cell lysates shown in FIG. 1). Thus, CD24 which is shedded from cells overexpressing CD24 (e.g., the pre-malignant adenomas cells or the malignant CRC tumor cells) can be detected by IP followed by Western blot analysis in serum samples. In addition, CD24 can be also traced in phases of bigger non-dissolved materials (vesicles and cell fragments) that are separated from their medium by ultra-centrifugation or sucrose gradient separation. Given that CD24 is anchored to the membrane and therefore might be present at the blood stream while is still integrated in membrane fragments or vesicles that are the product of cell blabbing, these large corpuses are concentrated as mentioned due to their high weight and, membranes are dissolved by lysis buffer, and IP is performed as described. Furthermore, antibodies to the protein might also be present in the sera of subjects who express high levels of CD24. Their presence might be detectable using ELISA methodology with plates, coated with the purified protein or fixed with cells that express high CD24 levels. HT29 cells that express high levels of CD24 are fixed to a 96 wells plate with 5% formaldehyde. Serum is added to the well for 2 hours incubation, after three washes, an anti-Human HRP antibody is added to the wells, washed five times, and a color reaction is performed by adding a substrate to the HRP for five minutes [3,3',5,5'-Tetramethylbenzidine (TMB), Sigma]. Reaction is stopped with sulfuric-acid and the color intensity (that stands for the amount of anti-CD24 antibody in the serum) is measured by an ELISA reader device at 450 nm. CD24 DNA that might be shed from the tumor cells to the blood-stream can be detected by performing RT PCR from peripheral blood. Mutations and polymorphisms that are searched for can be thus detected, and also by quantitative PCR reactions, amplifications in the CD24 genes that occur within the tumor cells can be seen.

The methods for detecting CD24 at the serum of subjects, as a tool for early diagnosis of cancer, can be applied for all tumors which were previously reported to have a tendency to over-express CD24. This includes all the following tumors, as well as their pre-malignant lesions, and other tumors that will be discovered in the future to over-express CD24. Most kinds of lymphomas over-express CD24, it was so far reported in: acute leukemia, Waldeyer's ring lymphomas, common acute lymphoblastic leukemia, non-Hodgkin lymphoma, hairy cell leukemia. Also, solid tumors express CD24 such as: clear cell sarcoma, nephroblastoma, renal cell carcinoma, adult mesoblastic nephroma, small-cell and non small-cell lung carcinoma, neuroblastoma, ganalioblastoma, sarcoma, squamous cell carcinoma, gastic and colorectal carcinoma, nasopharyngeal carcinoma, bladder cancer, breast cancer, glioma, ovarian cancer, prostate cancer, neuroendocrine prostate cancer, Merkel cell carcinoma and pancreatic cancer among others.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES

Additional References are Cited in Text

1. Aigner, S., Sthoeger, Z. M., Fogel, M., Weber, E., Zarn, J., Ruppert, M., Zeller, Y., Vestweber, D., Stahel, R., Sammar, M., and Altevogt, P. CD24, a mucin-type glycoprotein, is a ligand for P-selectin on human tumor cells. Blood, 1997, 89: 3385-3395.

2. Aigner, S., Ramos, C. L., Hafezi-Moghadam, A., Lawrence, M. B., Friederichs, J., Altevogt, P., and Ley, K. CD24 mediates rolling of breast carcinoma cells on P-selectin. FASEB J. 1998, 12: 1241-1251.

3. Baumann P, Cremers N, Kroese F, Orend G, Chiquet-Ehrismann R, Uede T, Yagita H, Sleeman J P. CD24 expression causes the acquisition of multiple cellular properties associated with tumor growth and metastasis. Cancer Res. 2005; 65:10783-93.

4. Kanaoka S, Yoshida K, Miura N, Sugimura H, Kajimura M. Potential usefulness of detecting cyclooxygenase 2 messenger RNA in feces for colorectal cancer screening. Gastroenterology. 2004; 127(2): 422-7.

5. Kristiansen et al., 2004; J. of Mol. Hist. 35: 255-262.

6. Laken S J, Petersen G M, Gruber S B, Oddoux, Vogelstein B. Familial colorectal cancer in Ashkenazim due to a hypermutable tract in APC. Nat Genet. 17: 79-83, 1997.

7. Mandel J, Bond J, et al., 1993, Reducing mortality from colorectal cancer by screening for fecal occult blood. Minnesota Colon Cancer Control Study. N Engl J Med 1993: 328: 1365-71.

8. McMahon P M, Bosch J L, et al., 2001. Cost-effectiveness of colorectal cancer screening. Radiology, 219(1): 44-50

9. Roessler M, Rollinger W, Palme S, Hagmann M L, et al., 2005. Identification of nicotinamide N-methyltransferase as a novel serum tumor marker for colorectal cancer. Clin Cancer Res. 2005 Sep. 15; 11(18):6550-7.

10. Roessler M., Rollinger W, Mantovani-Endl L., et al. Identification of PSME3 as a Novel Serum Tumor Marker for Colorectal Cancer by Combining Two-dimensional Polyacrylamide Gel Electrophoresis with a Strictly Mass Spectrometry-based Approach for Data Analysis. Molecular and Cellular Proteomics 5: 2092-2101, 2006.

11. Sagiv E., et al., 2006, Gastroenterology, 131: 630-639

12. Sammar, M., Aigner, S., Hubbe, M., Schirrmacher, V., Schachner, M., Vestweber, D., and Altevogt, P. Heat-stable antigen (CD24) as ligand for mouse P-selectin. Int. Immunol. 1994, 6: 1027-1036.

13. Schabath H, Runz S, Joumaa S, Altevogt P. CD24 affects CXCR4 function in pre-B lymphocytes and breast carcinoma cells. J Cell Sci. 2006; 119:314-25.

14. Smith S C, Oxford G, Wu Z, Nitz M D, Conaway M, Frierson H F, Hampton G, Theodorescu D. The metastasis-associated gene CD24 is regulated by Ral GTPase and is a mediator of cell proliferation and survival in human cancer. Cancer Res. 2006; 66:1917-22.

15. Strul, H., Barenboim, M, Leshno, M. Gartner, R. Kariv, E. Aljadeff, Y. Aljadeff, D. Kazanov, L. Strier, A. Keidar, Y. Knaani, Y. Degani, L. Alon-Baron, H. Sobol-Dvory, Z. Halpern, N. Arber. The I1307K adenomatous polyposis coli gene variant does not contribute in the assessment of the risk for colorectal cancer in Ashkenazi Jews. Cancer Epidemiol Biomarkers Prev 12:1012-1015, 2003

16. Weichert W., et al. 2005; Clin. Cancer Res. 11: 6574-6581.

17. Zhou Q., et al. 2003, Proc. Natl. Acad. Sci. 100: 15041-15046.

18. U.S. Pat. Appl. 20040005596 to Li J., et al.

What is claimed is:

1. A method of detecting CD24 in a stool sample of a subject, the method comprising:

(a) contacting the stool sample of the subject with an antibody which specifically binds CD24 under conditions which allow the formation of a complex comprising CD24 present in said stool sample and said antibody, wherein said stool sample is not subjected to cell lysis, wherein said CD24 comprised in said stool sample is not attached to intact cells, and wherein said antibody is labeled or conjugated to an enzyme; and (b) determining a presence and/or a level of said CD24 which is not attached to said intact cells in the stool sample, thereby detecting the CD24 in the stool sample of the subject.

2. The method of claim 1, wherein said CD24 is selected from the group consisting of shedded CD24, blebbed CD24 and soluble CD24.

3. The method of claim 1, wherein said antibody is fluorescently labeled.

4. The method of claim 1, wherein said antibody is radiolabeled.

5. The method of claim 1, wherein incubation of said enzyme with a chromogenic substrate produces a colorimetric reaction.

\* \* \* \* \*

SEQUENCE LISTING

```
<160> NUMBER OF SEQ ID NOS: 12

<210> SEQ ID NO 1
<211> LENGTH: 2194
<212> TYPE: DNA
<213> ORGANISM: Homo sapiens
<220> FEATURE:
<221> NAME/KEY: misc_feature
<222> LOCATION: (280)..(280)
<223> OTHER INFORMATION: C/T polymorphism

<400> SEQUENCE: 1
gggtctcgcc ggctcgccgc gctccccacc ttgcctgcgc ccgcccggag ccagcggttc      60
tccaagcacc cagcatcctg ctagacgcgc cgcgcaccga cggaggggac atgggcagag     120
caatggtggc caggctcggg ctggggctgc tgctgctggc actgctccta cccacgcaga     180
tttattccag tgaaacaaca actggaactt caagtaactc ctcccagagt acttccaact     240
ctgggttggc cccaaatcca actaatgcca ccaccaaggn ggctggtggt gccctgcagt     300
caacagccga tctcttcgtg gtctcactct ctcttctgca tctctactct taagagactc     360
aggccaagaa acgtcttcta aatttcccca tcttctaaac ccaatccaaa tggcgtctgg     420
aagtccaatg tggcaaggaa aaacaggtct tcatcgaatc tactaattcc acaccttta      480 ttgacacaga aaatgttgag aatcccaaat ttgattgatt tgaagaacat gtgagaggtt     540
tgactagatg atggatgcca atattaaatc tgctggagtt tcatgtacaa gatgaaggag     600
aggcaacatc caaaatagtt aagacatgat ttccttgaat gtggcttgag aaatatggac     660
acttaatact accttgaaaa taagaataga aataaaggat gggattgtgg aatggagatt     720
cagttttcat ttggttcatt aattctataa ggccataaaa caggtaatat aaaaagcttc     780
catgattcta tttatatgta catgagaagg aacttccagg tgttactgta attcctcaac     840
gtattgtttc gacagcacta atttaatgcc gatatactct agatgaagtt ttacattgtt     900
gagctattgc tgttctcttg ggaactgaac tcactttcct cctgaggctt tggatttgac     960
attgcatttg acctttatg tagtaattga catgtgccag ggcaatgatg aatgagaatc    1020 taccccaga tccaagcatc ctgagcaact cttgattatc catattgagt caaatggtag    1080
gcatttccta tcacctgttt ccattcaaca agagcactac attcatttag ctaaacggat    1140
tccaaagagt agaattgcat tgaccacgac taatttcaaa atgctttta ttattattat     1200 tttttagaca gtctcacttt gtcgcccagg ccggagtgca gtggtgcgat ctcagatcag    1260
tgtaccattt gcctcccggg ctcaagcgat tctcctgcct cagcctccca agtagctggg    1320
attacaggca cctgccacca tgcccggcta attttgtaa tttttagtaga gcagggtttc     1380 caccatgttg cccaggctgg tttcgaactc ctgacctcag gtgatccacc cgcctcggcc    1440
tcccaaagtg ctgggattac aggcttgagc ccccgcgccc agccatcaaa atgcttttta    1500
tttctgcata tgttgaatac tttttacaat ttaaaaaat gatctgtttt gaaggcaaaa     1560
ttgcaaatct tgaaattaag aaggcaaaaa tgtaaaggag tcaaaactat aaatcaagta    1620
```

```
tttgggaagt gaagactgga agctaatttg cattaaattc acaaactttt atactctttc    1680
tgtatataca ttttttttct ttaaaaaaca actatggatc agaatagcca catttagaac    1740 acttttgtt  atcagtcaat attttagat  agttagaacc tggtcctaag cctaaaagtg    1800
ggcttgattc tgcagtaaat cttttacaac tgcctcgaca cacataaacc ttttaaaaa    1860 tagacactcc ccgaagtctt tgttcgcat ggtcacacac tgatgcttag atgttccagt    1920
aatctaatat ggccacagta gtcttgatga ccaaagtcct ttttttccat ctttagaaaa    1980
ctacatggga acaaacagat cgaacagttt tgaagctact gtgtgtgtga atgaacactc    2040
ttgctttatt ccagaatgct gtacatctat tttggattgt atattgtgtt tgtgtattta    2100
cgctttgatt catagtaact tcttatggaa ttgatttgca ttgaacacaa actgtaaata    2160 aaagaaatg  gctgaaagag caaaaaaaa  aaaa                                2194
```

<210> SEQ ID NO 2
<211> LENGTH: 80
<212> TYPE: PRT
<213> ORGANISM: Homo sapiens
<220> FEATURE:
<221> NAME/KEY: misc_feature
<222> LOCATION: (57)..(57)
<223> OTHER INFORMATION: Ala / Val polymorphism

<400> SEQUENCE: 2

```
Met Gly Arg Ala Met Val Ala Arg Leu Gly Leu Gly Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Xaa Ala Gly Gly Ala Leu Gln Ser
    50                  55                  60

Thr Ala Ser Leu Phe Val Val Ser Leu Ser Leu Leu His Leu Tyr Ser
65                  70                  75                  80
```

<210> SEQ ID NO 3
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 3

```
ttgttgccac ttggcatttt tgaggc                                          26
```

<210> SEQ ID NO 4
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 4

```
ggattgggtt tagaagatgg ggaaa                                           25
```

<210> SEQ ID NO 5
<211> LENGTH: 27
<212> TYPE: DNA
<213> ORGANISM: Artificial sequence
<220> FEATURE:
<223> OTHER INFORMATION: Single strand DNA oligonucleotide

```
<400> SEQUENCE: 5
gattctgcta ataccctgca aatagca                                              27

<210> SEQ ID NO 6
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 6
ccctgcagtc tgctggattt gg                                                   22

<210> SEQ ID NO 7
<211> LENGTH: 10719
<212> TYPE: DNA
<213> ORGANISM: Homo sapiens
<220> FEATURE:
<221> NAME/KEY: misc_feature
<222> LOCATION: (3977)..(3977)
<223> OTHER INFORMATION: T/A polymorphism
<220> FEATURE:
<221> NAME/KEY: misc_feature
<222> LOCATION: (4006)..(4006)
<223> OTHER INFORMATION: G/C polymorphism

<400> SEQUENCE: 7
tggagacaga atggaggtgc tgccggactc ggaaatgggg tccaagggta gccaaggatg      60
gctgcagctt catatgatca gttgttaaag caagttgagg cactgaagat ggagaactca     120
aatcttcgac aagagctaga agataattcc aatcatctta caaaactgga aactgaggca     180
tctaatatga aggaagtact taaacaacta caaggaagta ttgaagatga agctatggct     240
tcttctggac agattgattt attagagcgt cttaaagagc ttaacttaga tagcagtaat     300
ttccctggag taaaactgcg gtcaaaaatg tccctccgtt cttatggaag ccgggaagga     360
tctgtatcaa gccgttctgg agagtgcagt cctgttccta tgggttcatt ccaagaaga     420 gggtttgtaa atggaagcag agaaagtact ggatatttag aagaacttga aaagagagg     480 tcattgcttc ttgctgatct tgacaaagaa gaaaaggaaa aagactggta ttacgctcaa     540
cttcagaatc tcactaaaag aatagatagt cttccttaa ctgaaaattt tccttacaa      600 acagatatga ccagaaggca attggaatat gaagcaaggc aaatcagagt tgcgatggaa     660
gaacaactag gtacctgcca ggatatggaa aaacgagcac agcgaagaat agccagaatt     720
cagcaaatcg aaaaggacat acttcgtata cgacagcttt tacagtccca agcaacagaa     780
gcagagaggt catctcagaa caagcatgaa accggctcac atgatgctga gcggcagaat     840
gaaggtcaag gagtgggaga atcaacatg gcaacttctg gtaatggtca gggttcaact     900
acacgaatgg accatgaaac agccagtgtt ttgagttcta gtagcacaca ctctgcacct     960
cgaaggctga caagtcatct ggaaccaag gtggaaatgg tgtattcatt gttgtcaatg    1020
cttggtactc atgataagga tgatatgtcg cgaactttgc tagctatgtc tagctcccaa    1080
gacagctgta tatccatgcg acagtctgga tgtcttcctc tcctcatcca gcttttacat    1140
ggcaatgaca agactctgt attgttggga aattcccggg cagtaaaga ggctcgggcc     1200 agggccagtg cagcactcca caacatcatt cactcacagc ctgatgacaa agagaggcagg    1260 cgtgaaatcc gagtccttca tcttttggaa cagatacgcg cttactgtga aacctgttgg    1320
gagtggcagg aagctcatga accaggcatg gaccaggaca aaaatccaat gccagctcct    1380
gttgaacatc agatctgtcc tgctgtgtgt gttctaatga aactttcatt tgatgaagag    1440
```

```
catagacatg caatgaatga actaggggga ctacaggcca ttgcagaatt attgcaagtg   1500
gactgtgaaa tgtatgggct tactaatgac cactacagta ttacactaag acgatatgct   1560
ggaatggctt tgacaaactt gacttttgga gatgtagcca acaaggctac gctatgctct   1620
atgaaaggct gcatgagagc acttgtggcc caactaaaat ctgaaagtga agacttacag   1680
caggttattg cgagtgtttt gaggaatttg tcttggcgag cagatgtaaa tagtaaaaag   1740
acgttgcgag aagttggaag tgtgaaagca ttgatgaat gtgctttaga agttaaaaag   1800
gaatcaaccc tcaaaagcgt attgagtgcc ttatggaatt tgtcagcaca ttgcactgag   1860
aataaagcta atatatgtgc tgtagatggt gcacttgcat ttttggttgg cactcttact   1920
taccggagcc agacaaacac tttagccatt attgaaagtg gaggtgggat attacggaat   1980
gtgtccagct tgatagctac aaatgaggac cacaggcaaa tcctaagaga gaacaactgt   2040
ctacaaactt tattacaaca cttaaaatct catagtttga caatagtcag taatgcatgt   2100
ggaactttgt ggaatctctc agcaagaaat cctaaagacc aggaagcatt atgggacatg   2160
ggggcagtta gcatgctcaa gaacctcatt cattcaaagc acaaaatgat tgctatggga   2220
agtgctgcag ctttaaggaa tctcatggca ataggcctg cgaagtacaa ggatgccaat   2280
attatgtctc ctggctcaag cttgccatct cttcatgtta ggaaacaaaa agccctagaa   2340
gcagaattag atgctcagca cttatcagaa acttttgaca atatagacaa tttaagtccc   2400
aaggcatctc atcgtagtaa gcagagacac aagcaaagtc tctatggtga ttatgttttt   2460
gacaccaatc gacatgatga taataggtca gacaatttta atactggcaa catgactgtc   2520
ctttcaccat atttgaatac tacagtgtta cccagctcct cttcatcaag aggaagctta   2580
gatagttctc gttctgaaaa agatagaagt ttggagagag aacgcggaat tggtctaggc   2640
aactaccatc cagcaacaga aaatccagga acttcttcaa agcgaggttt gcagatctcc   2700
accactgcag cccagattgc caaagtcatg gaagaagtgt cagccattca tacctctcag   2760
gaagacagaa gttctgggtc taccactgaa ttacattgtg tgacagatga gagaaatgca   2820
cttagaagaa gctctgctgc ccatacacat tcaaacactt acaatttcac taagtcggaa   2880
aattcaaata ggacatgttc tatgccttat gccaaattag aatacaagag atcttcaaat   2940
gatagtttaa atagtgtcag tagtagtgat ggttatggta aaagaggtca aatgaaaccc   3000
tcgattgaat cctattctga agatgatgaa agtaagtttt gcagttatgg tcaataccca   3060
gccgacctag cccataaaat acatagtgca aatcatatgg atgataatga tggagaacta   3120
gatacaccaa taaattatag tcttaaatat tcagatgagc agttgaactc tggaaggcaa   3180
agtccttcac agaatgaaag atgggcaaga cccaaacaca taatagaaga tgaaataaaa   3240
caaagtgagc aaagacaatc aaggaatcaa agtacaactt atcctgttta tactgagagc   3300
actgatgata aacacctcaa gttccaacca cattttggac agcaggaatg tgtttctcca   3360
tacaggtcac ggggagccaa tggttcagaa acaaatcgag tgggttctaa tcatggaatt   3420
aatcaaaatg taagccagtc tttgtgtcaa gaagatgact atgaagatga taagcctacc   3480
aattatagtg aacgttactc tgaagaagaa cagcatgaag aagaagagag accaacaaat   3540
tatagcataa aatataatga agagaaacgt catgtggatc agcctattga ttatagttta   3600
aaatatgcca cagatattcc ttcatcacag aaacagtcat tttcattctc aaagagttca   3660
tctggacaaa gcagtaaaac cgaacatatg tcttcaagca gtgagaatac gtccacacct   3720
tcatctaatg ccaagaggca gaatcagctc catccaagtt ctgcacagag tagaagtggt   3780
```

```
cagcctcaaa aggctgccac ttgcaaagtt tcttctatta accaagaaac aatacagact    3840
tattgtgtag aagatactcc aatatgtttt tcaagatgta gttcattatc atctttgtca    3900
tcagctgaag atgaaatagg atgtaatcag acgacacagg aagcagattc tgctaatacc    3960
ctgcaaatag cagaaanaaa agaaaagatt ggaactaggt cagctnaaga tcctgtgagc    4020
gaagttccag cagtgtcaca gcaccctaga accaaatcca gcagactgca gggttctagt    4080
ttatcttcag aatcagccag gcacaaagct gttgaatttt cttcaggagc gaaatctccc    4140
tccaaaagtg gtgctcagac acccaaaagt ccacctgaac actatgttca ggagacccca    4200
ctcatgttta gcagatgtac ttctgtcagt tcacttgata gttttgagag tcgttcgatt    4260
gccagctccg ttcagagtga accatgcagt ggaatggtaa gtggcattat aagcccagt    4320
gatcttccag atagccctgg acaaaccatg ccaccaagca gaagtaaaac acctccacca    4380
cctcctcaaa cagctcaaac caagcgagaa gtacctaaaa ataaagcacc tactgctgaa    4440
aagagagaga gtggacctaa gcaagctgca gtaaatgctg cagttcagag ggtccaggtt    4500
cttccagatg ctgatacttt attacatttt gccacgaaaa gtactccaga tggattttct    4560
tgttcatcca gcctgagtgc tctgagcctc gatgagccat ttatacagaa agatgtggaa    4620
ttaagaataa tgcctccagt tcaggaaaat gacaatggga atgaaacaga atcagagcag    4680
cctaaagaat caaatgaaaa ccaagagaaa gaggcagaaa aaactattga ttctgaaaag    4740
gacctattag atgattcaga tgatgatgat attgaaatac tagaagaatg tattatttct    4800
gccatgccaa caaagtcatc acgtaaagca aaaaagccag cccagactgc ttcaaaatta    4860
cctccacctg tggcaaggaa accaagtcag ctgcctgtgt acaaacttct accatcacaa    4920
aacaggttgc aaccccaaaa gcatgttagt tttacaccgg gggatgatat gccacgggtg    4980
tattgtgttg aagggacacc tataaacttt tccacagcta catctctaag tgatctaaca    5040
atcgaatccc ctccaaatga gttagctgct ggagaaggag ttagaggagg ggcacagtca    5100
ggtgaatttg aaaaacgaga taccattcct acagaaggca aagtacaga tgaggctcaa    5160
ggaggaaaaa cctcatctgt aaccatacct gaattggatg acaataaagc agaggaaggt    5220
gatattcttg cagaatgcat taattctgct atgcccaaag ggaaaagtca caagcctttc    5280
cgtgtgaaaa agataatgga ccaggtccag caagcatctg cgtcttcttc tgcacccaac    5340
aaaaatcagt tagatggtaa gaaaagaaa ccaacttcac cagtaaaacc tataccacaa    5400
aatactgaat ataggacacg tgtaagaaaa aatgcagact caaaaaataa tttaaatgct    5460
gagagagttt tctcagacaa caaagattca aagaaacaga atttgaaaaa taattccaag    5520
gtcttcaatg ataagctccc aaataatgaa gatagagtca gaggaagttt tgcttttgat    5580
tcacctcatc attacacgcc tattgaagga actccttact gtttttcacg aaatgattct    5640
ttgagttctc tagattttga tgatgatgat gttgacctt ccagggaaaa ggctgaatta    5700
agaaaggcaa agaaaataa ggaatcgag gctaaagtta ccagccacac agaactaacc    5760
tccaaccaac aatcagctaa taagacacaa gctattgcaa agcagccaat aaatcgaggt    5820
cagcctaaac ccatacttca gaaacaatcc acttttcccc agtcatccaa agacatacca    5880
gacagagggg cagcaactga tgaaaagtta cagaattttg ctattgaaaa tactccggtt    5940
tgcttttctc ataattcctc tctgagttct ctcagtgaca ttgaccaaga aacaacaat    6000
aaagaaaatg aacctatcaa agagactgag cccctgact cacagggaga accaagtaaa    6060
cctcaagcat caggctatgc tcctaaatca tttcatgttg aagatacccc agtttgtttc    6120
tcaagaaaca gttctctcag ttctcttagt attgactctg aagatgacct gttgcaggaa    6180
```

```
tgtataagct ccgcaatgcc aaaaaagaaa aagccttcaa gactcaaggg tgataatgaa    6240
aaacatagtc ccagaaatat gggtggcata ttaggtgaag atctgacact tgatttgaaa    6300
gatatacaga gaccagattc agaacatggt ctatccctg attcagaaaa ttttgattgg     6360
aaagctattc aggaaggtgc aaattccata gtaagtagtt tacatcaagc tgctgctgct    6420
gcatgtttat ctagacaagc ttcgtctgat tcagattcca tcctttccct gaaatcagga    6480
atctctctgg gatcaccatt tcatcttaca cctgatcaag aagaaaaacc ctttacaagt    6540
aataaaggcc cacgaattct aaaaccaggg gagaaaagta cattggaaac taaaaagata    6600
gaatctgaaa gtaaaggaat caaggagga aaaaagttt ataaagttt gattactgga       6660 aaagttcgat ctaattcaga aatttcaggc caaatgaaac agccccttca agcaaacatg    6720
ccttcaatct ctcgaggcag acaatgatt catattccag gagttcgaaa tagctcctca     6780
agtacaagtc ctgtttctaa aaaggcccca ccccttaaga ctccagcctc caaaagccct    6840
agtgaaggtc aaacagccac cacttctcct agaggagcca agccatctgt gaaatcagaa    6900
ttaagccctg ttgccaggca gacatcccaa ataggtgggt caagtaaagc accttctaga    6960
tcaggatcta gagattcgac cccttcaaga cctgcccagc aaccattaag tagacctata    7020
cagtctcctg gccgaaactc aatttcccct ggtagaaatg gaataagtcc tcctaacaaa    7080
ttatctcaac ttccaaggac atcatcccct agtactgctt caactaagtc ctcaggttct    7140
ggaaaaatgt catatacatc tccaggtaga cagatgagcc aacagaacct taccaaacaa    7200
acaggtttat ccaagaatgc cagtagtatt ccaagaagtg agtctgcctc caaaggacta    7260
aatcagatga ataatggtaa tggagccaat aaaaaggtag aactttctag aatgtcttca    7320
actaaatcaa gtggaagtga atctgataga tcagaaagac ctgtattagt acgccagtca    7380
actttcatca aagaagctcc aagcccaacc ttaagaagaa aattggagga atctgcttca    7440
tttgaatctc tttctccatc atctagacca gcttctccca ctaggtccca ggcacaaact    7500
ccagttttaa gtccttccct tcctgatatg tctctatcca cacattcgtc tgttcaggct    7560
ggtggatggc gaaaactccc acctaatctc agtcccacta tagagtataa tgatggaaga    7620
ccagcaaagc gccatgatat tgcacggtct cattctgaaa gtccttctag acttccaatc    7680
aataggtcag gaacctggaa acgtgagcac agcaaacatt catcatccct tcctcgagta    7740
agcacttgga gaagaactgg aagttcatct tcaattcttt ctgcttcatc agaatccagt    7800
gaaaaagcaa aaagtgagga tgaaaaacat gtgaactcta tttcaggaac caaacaaagt    7860
aaagaaaacc aagtatccgc aaaaggaaca tggagaaaaa taaagaaaa tgaattttct     7920 cccacaaata gtacttctca gaccgttcc tcaggtgcta caaatggtgc tgaatcaaag     7980
actctaattt atcaaatggc acctgctgtt tctaaaacag aggatgttg ggtgagaatt      8040 gaggactgtc ccattaacaa tcctagatct ggaagatctc ccacaggtaa tactcccccg    8100
gtgattgaca gtgtttcaga aaaggcaaat ccaaacatta agattcaaa agataatcag      8160 gcaaaacaaa atgtgggtaa tggcagtgtt cccatgcgta ccgtgggttt ggaaaatcgc    8220
ctgaactcct ttattcaggt ggatgcccct gaccaaaaag gaactgagat aaaaccagga    8280
caaaataatc ctgtccctgt atcagagact aatgaaagtt ctatagtgga acgtaccca     8340 ttcagttcta gcagctcaag caaacacagt tcacctagtg ggactgttgc tgccagagtg    8400 actccttta attacaaccc aagcctagg aaaagcagcg cagatagcac ttcagctcgg      8460
ccatctcaga tcccaactcc agtgaataac aacacaaaga agcgagattc caaaactgac    8520
```

-continued

```
agcacagaat ccagtggaac ccaaagtcct aagcgccatt ctgggtctta ccttgtgaca   8580
tctgtttaaa agagaggaag aatgaaacta agaaaattct atgttaatta caactgctat   8640
atagacattt tgtttcaaat gaaactttaa aagactgaaa aattttgtaa ataggtttga   8700
ttcttgttag agggtttttg ttctggaagc catatttgat agtatacttt gtcttcactg   8760
gtcttatttt gggaggcact cttgatggtt aggaaaaaaa tagtaaagcc aagtatgttt   8820
gtacagtatg ttttacatgt atttaaagta gcatcccatc ccaacttcct ttaattattg   8880
cttgtcttaa aataatgaac actacagata gaaaatatga tatattgctg ttatcaatca   8940
tttctagatt ataaactgac taaacttaca tcagggaaaa attggtattt atgcaaaaaa   9000
aaatgttttt gtccttgtga gtccatctaa catcataatt aatcatgtgg ctgtgaaatt   9060
cacagtaata tggttcccga tgaacaagtt tacccagcct gctttgcttt actgcatgaa   9120
tgaaactgat ggttcaattt cagaagtaat gattaacagt tatgtggtca catgatgtgc   9180
atagagatag ctacagtgta ataatttaca ctattttgtg ctccaaacaa aacaaaaatc   9240
tgtgtaactg taaaacattg aatgaaacta ttttacctga actagatttt atctgaaagt   9300
aggtagaatt tttgctatgc tgtaatttgt tgtatattct ggtatttgag gtgagatggc   9360
tgctctttta ttaatgagac atgaattgtg tctcaacaga aactaaatga acatttcaga   9420
ataaattatt gctgtatgta aactgttact gaaattggta tttgtttgaa gggtcttgtt   9480
tcacatttgt attaataatt gtttaaaatg cctcttttaa aagcttatat aaattttttt   9540
cttcagcttc tatgcattaa gagtaaaatt cctcttactg taataaaaac aattgaagaa   9600
gactgttgcc acttaaccat tccatgcgtt ggcacttatc tattcctgaa atttctttta   9660
tgtgattagc tcatcttgat ttttaatatt tttccactta aacttttttt tcttactcca   9720
ctggagctca gtaaaagtaa attcatgtaa tagcaatgca agcagcctag cacagactaa   9780
gcattgagca taataggccc acataatttc ctctttctta atattataga attctgtact   9840
tgaaattgat tcttagacat tgcagtctct tcgaggcttt acagtgtaaa ctgtcttgcc   9900
ccttcatctt cttgttgcaa ctgggtctga catgaacact ttttatcacc ctgtatgtta   9960
gggcaagatc tcagcagtga agtataatca gcactttgcc atgctcagaa aattcaaatc  10020
acatggaact ttagaggtag atttaatacg attaagatat tcagaagtat attttagaat  10080
ccctgcctgt taaggaaact ttatttgtgg taggtacagt tctggggtac atgttaagtg  10140
tccccttata cagtggaggg aagtcttcct tcctgaagga aaataaactg acacttatta  10200
actaagataa tttacttaat atatcttccc tgatttgttt taaaagatca gagggtgact  10260
gatgatacat gcatacatat ttgttgaata aatgaaaatt tatttttagt gataagattc  10320
atacactctg tatttgggga gggaaaacct ttttaagcat ggtggggcac tcagatagga  10380
gtgaatacac ctacctggtg ccttgaaaat cacatcaagt agttaattat ctacccctta  10440
cctgtgttta taacttccag gtaatgagaa tgattttttt taaagctaaa atgccagtaa  10500
ataaaagtgc tatgacttga gctaagatat ttgactccaa tgcctgtact gtgtctactg  10560
caccactttg taaacacttc aatttactat ctttgaaatg attgaccttt aaatttttgc  10620
caaatgttat ctgaaattgt ctatgaatac catctacttc tgttgttttc ccaggcttcc  10680
ataaacaatg gagatacatg caaaaaaaaa aaaaaaaaa                         10719
```

<210> SEQ ID NO 8
<211> LENGTH: 2843
<212> TYPE: PRT
<213> ORGANISM: Homo sapiens

```
<220> FEATURE:
<221> NAME/KEY: misc_feature
<222> LOCATION: (1307)..(1307)
<223> OTHER INFORMATION: Ile / lys polymorphism
<220> FEATURE:
<221> NAME/KEY: misc_feature
<222> LOCATION: (1317)..(1317)
<223> OTHER INFORMATION: Glu / Gln polymorphism

<400> SEQUENCE: 8
```

| | | | | | | | | | | | | | | | |
|---|---|---|---|---|---|---|---|---|---|---|---|---|---|---|---|
| Met | Ala | Ala | Ala | Ser | Tyr | Asp | Gln | Leu | Leu | Lys | Gln | Val | Glu | Ala | Leu |
| 1 | | | | 5 | | | | | 10 | | | | | 15 | |
| Lys | Met | Glu | Asn | Ser | Asn | Leu | Arg | Gln | Glu | Leu | Glu | Asp | Asn | Ser | Asn |
| | | | 20 | | | | | 25 | | | | | 30 | | |
| His | Leu | Thr | Lys | Leu | Glu | Thr | Glu | Ala | Ser | Asn | Met | Lys | Glu | Val | Leu |
| | | | 35 | | | | 40 | | | | | 45 | | | |
| Lys | Gln | Leu | Gln | Gly | Ser | Ile | Glu | Asp | Glu | Ala | Met | Ala | Ser | Ser | Gly |
| 50 | | | | | 55 | | | | | 60 | | | | | |
| Gln | Ile | Asp | Leu | Leu | Glu | Arg | Leu | Lys | Glu | Leu | Asn | Leu | Asp | Ser | Ser |
| 65 | | | | | 70 | | | | | 75 | | | | | 80 |
| Asn | Phe | Pro | Gly | Val | Lys | Leu | Arg | Ser | Lys | Met | Ser | Leu | Arg | Ser | Tyr |
| | | | | 85 | | | | | 90 | | | | | 95 | |
| Gly | Ser | Arg | Glu | Gly | Ser | Val | Ser | Ser | Arg | Ser | Gly | Glu | Cys | Ser | Pro |
| | | | 100 | | | | | 105 | | | | | 110 | | |
| Val | Pro | Met | Gly | Ser | Phe | Pro | Arg | Arg | Gly | Phe | Val | Asn | Gly | Ser | Arg |
| | | 115 | | | | | 120 | | | | | 125 | | | |
| Glu | Ser | Thr | Gly | Tyr | Leu | Glu | Glu | Leu | Glu | Lys | Glu | Arg | Ser | Leu | Leu |
| 130 | | | | | 135 | | | | | 140 | | | | | |
| Leu | Ala | Asp | Leu | Asp | Lys | Glu | Glu | Lys | Glu | Lys | Asp | Trp | Tyr | Tyr | Ala |
| 145 | | | | | 150 | | | | | 155 | | | | | 160 |
| Gln | Leu | Gln | Asn | Leu | Thr | Lys | Arg | Ile | Asp | Ser | Leu | Pro | Leu | Thr | Glu |
| | | | | 165 | | | | | 170 | | | | | 175 | |
| Asn | Phe | Ser | Leu | Gln | Thr | Asp | Met | Thr | Arg | Arg | Gln | Leu | Glu | Tyr | Glu |
| | | | 180 | | | | | 185 | | | | | 190 | | |
| Ala | Arg | Gln | Ile | Arg | Val | Ala | Met | Glu | Glu | Gln | Leu | Gly | Thr | Cys | Gln |
| | | 195 | | | | | 200 | | | | | 205 | | | |
| Asp | Met | Glu | Lys | Arg | Ala | Gln | Arg | Arg | Ile | Ala | Arg | Ile | Gln | Gln | Ile |
| 210 | | | | | 215 | | | | | 220 | | | | | |
| Glu | Lys | Asp | Ile | Leu | Arg | Ile | Arg | Gln | Leu | Leu | Gln | Ser | Gln | Ala | Thr |
| 225 | | | | | 230 | | | | | 235 | | | | | 240 |
| Glu | Ala | Glu | Arg | Ser | Ser | Gln | Asn | Lys | His | Glu | Thr | Gly | Ser | His | Asp |
| | | | | 245 | | | | | 250 | | | | | 255 | |
| Ala | Glu | Arg | Gln | Asn | Glu | Gly | Gln | Gly | Val | Gly | Glu | Ile | Asn | Met | Ala |
| | | | 260 | | | | | 265 | | | | | 270 | | |
| Thr | Ser | Gly | Asn | Gly | Gln | Gly | Ser | Thr | Thr | Arg | Met | Asp | His | Glu | Thr |
| | | 275 | | | | | 280 | | | | | 285 | | | |
| Ala | Ser | Val | Leu | Ser | Ser | Ser | Thr | His | Ser | Ala | Pro | Arg | Arg | Leu |  |
| | | 290 | | | | | 295 | | | | | 300 | | | |
| Thr | Ser | His | Leu | Gly | Thr | Lys | Val | Glu | Met | Val | Tyr | Ser | Leu | Leu | Ser |
| 305 | | | | | 310 | | | | | 315 | | | | | 320 |
| Met | Leu | Gly | Thr | His | Asp | Lys | Asp | Asp | Met | Ser | Arg | Thr | Leu | Leu | Ala |
| | | | | 325 | | | | | 330 | | | | | 335 | |
| Met | Ser | Ser | Ser | Gln | Asp | Ser | Cys | Ile | Ser | Met | Arg | Gln | Ser | Gly | Cys |
| | | | 340 | | | | | 345 | | | | | 350 | | |
| Leu | Pro | Leu | Leu | Ile | Gln | Leu | Leu | His | Gly | Asn | Asp | Lys | Asp | Ser | Val |
| | | | 355 | | | | | 360 | | | | | 365 | | |

-continued

```
Leu Leu Gly Asn Ser Arg Gly Ser Lys Glu Ala Arg Ala Arg Ala Ser
        370                 375                 380
Ala Ala Leu His Asn Ile Ile His Ser Gln Pro Asp Asp Lys Arg Gly
385                 390                 395                 400
Arg Arg Glu Ile Arg Val Leu His Leu Leu Glu Gln Ile Arg Ala Tyr
                405                 410                 415
Cys Glu Thr Cys Trp Glu Trp Gln Glu Ala His Glu Pro Gly Met Asp
            420                 425                 430
Gln Asp Lys Asn Pro Met Pro Ala Pro Val Glu His Gln Ile Cys Pro
        435                 440                 445
Ala Val Cys Val Leu Met Lys Leu Ser Phe Asp Glu His Arg His
450                 455                 460
Ala Met Asn Glu Leu Gly Gly Leu Gln Ala Ile Ala Glu Leu Leu Gln
465                 470                 475                 480
Val Asp Cys Glu Met Tyr Gly Leu Thr Asn Asp His Tyr Ser Ile Thr
                485                 490                 495
Leu Arg Arg Tyr Ala Gly Met Ala Leu Thr Asn Leu Thr Phe Gly Asp
            500                 505                 510
Val Ala Asn Lys Ala Thr Leu Cys Ser Met Lys Gly Cys Met Arg Ala
        515                 520                 525
Leu Val Ala Gln Leu Lys Ser Glu Ser Glu Asp Leu Gln Gln Val Ile
530                 535                 540
Ala Ser Val Leu Arg Asn Leu Ser Trp Arg Ala Asp Val Asn Ser Lys
545                 550                 555                 560
Lys Thr Leu Arg Glu Val Gly Ser Val Lys Ala Leu Met Glu Cys Ala
                565                 570                 575
Leu Glu Val Lys Lys Glu Ser Thr Leu Lys Ser Val Leu Ser Ala Leu
            580                 585                 590
Trp Asn Leu Ser Ala His Cys Thr Glu Asn Lys Ala Asp Ile Cys Ala
        595                 600                 605
Val Asp Gly Ala Leu Ala Phe Leu Val Gly Thr Leu Thr Tyr Arg Ser
610                 615                 620
Gln Thr Asn Thr Leu Ala Ile Ile Glu Ser Gly Gly Gly Ile Leu Arg
625                 630                 635                 640
Asn Val Ser Ser Leu Ile Ala Thr Asn Glu Asp His Arg Gln Ile Leu
                645                 650                 655
Arg Glu Asn Asn Cys Leu Gln Thr Leu Leu Gln His Leu Lys Ser His
            660                 665                 670
Ser Leu Thr Ile Val Ser Asn Ala Cys Gly Thr Leu Trp Asn Leu Ser
        675                 680                 685
Ala Arg Asn Pro Lys Asp Gln Glu Ala Leu Trp Asp Met Gly Ala Val
690                 695                 700
Ser Met Leu Lys Asn Leu Ile His Ser Lys His Lys Met Ile Ala Met
705                 710                 715                 720
Gly Ser Ala Ala Ala Leu Arg Asn Leu Met Ala Asn Arg Pro Ala Lys
                725                 730                 735
Tyr Lys Asp Ala Asn Ile Met Ser Pro Gly Ser Ser Leu Pro Ser Leu
            740                 745                 750
His Val Arg Lys Gln Lys Ala Leu Glu Ala Glu Leu Asp Ala Gln His
        755                 760                 765
Leu Ser Glu Thr Phe Asp Asn Ile Asp Asn Leu Ser Pro Lys Ala Ser
770                 775                 780
```

-continued

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
            805                 810                 815

Gly Asn Met Thr Val Leu Ser Pro Tyr Leu Asn Thr Thr Val Leu Pro
        820                 825                 830

Ser Ser Ser Ser Ser Arg Gly Ser Leu Asp Ser Ser Arg Ser Glu Lys
    835                 840                 845

Asp Arg Ser Leu Glu Arg Glu Arg Gly Ile Gly Leu Gly Asn Tyr His
850                 855                 860

Pro Ala Thr Glu Asn Pro Gly Thr Ser Ser Lys Arg Gly Leu Gln Ile
865                 870                 875                 880

Ser Thr Thr Ala Ala Gln Ile Ala Lys Val Met Glu Glu Val Ser Ala
            885                 890                 895

Ile His Thr Ser Gln Glu Asp Arg Ser Ser Gly Ser Thr Thr Glu Leu
                900                 905                 910

His Cys Val Thr Asp Glu Arg Asn Ala Leu Arg Arg Ser Ser Ala Ala
            915                 920                 925

His Thr His Ser Asn Thr Tyr Asn Phe Thr Lys Ser Glu Asn Ser Asn
930                 935                 940

Arg Thr Cys Ser Met Pro Tyr Ala Lys Leu Glu Tyr Lys Arg Ser Ser
945                 950                 955                 960

Asn Asp Ser Leu Asn Ser Val Ser Ser Asp Gly Tyr Gly Lys Arg
                965                 970                 975

Gly Gln Met Lys Pro Ser Ile Glu Ser Tyr Ser Glu Asp Asp Glu Ser
            980                 985                 990

Lys Phe Cys Ser Tyr Gly Gln Tyr Pro Ala Asp Leu Ala His Lys Ile
            995                 1000                1005

His Ser Ala Asn His Met Asp Asp Asp Gly Glu Leu Asp Thr
    1010                1015                1020

Pro Ile Asn Tyr Ser Leu Lys Tyr Ser Asp Glu Gln Leu Asn Ser
    1025                1030                1035

Gly Arg Gln Ser Pro Ser Gln Asn Glu Arg Trp Ala Arg Pro Lys
    1040                1045                1050

His Ile Ile Glu Asp Glu Ile Lys Gln Ser Glu Gln Arg Gln Ser
    1055                1060                1065

Arg Asn Gln Ser Thr Thr Tyr Pro Val Tyr Thr Glu Ser Thr Asp
    1070                1075                1080

Asp Lys His Leu Lys Phe Gln Pro His Phe Gly Gln Gln Glu Cys
    1085                1090                1095

Val Ser Pro Tyr Arg Ser Arg Gly Ala Asn Gly Ser Glu Thr Asn
    1100                1105                1110

Arg Val Gly Ser Asn His Gly Ile Asn Gln Asn Val Ser Gln Ser
    1115                1120                1125

Leu Cys Gln Glu Asp Asp Tyr Glu Asp Asp Lys Pro Thr Asn Tyr
    1130                1135                1140

Ser Glu Arg Tyr Ser Glu Glu Gln His Glu Glu Glu Arg
    1145                1150                1155

Pro Thr Asn Tyr Ser Ile Lys Tyr Asn Glu Glu Lys Arg His Val
    1160                1165                1170

Asp Gln Pro Ile Asp Tyr Ser Leu Lys Tyr Ala Thr Asp Ile Pro
    1175                1180                1185

Ser Ser Gln Lys Gln Ser Phe Ser Phe Ser Lys Ser Ser Ser Gly

```
                    1190                1195                 1200
Gln Ser  Ser Lys Thr Glu  His Met Ser Ser  Ser Glu Asn Thr
         1205                1210                1215

Ser Thr  Pro Ser Ser Asn  Ala Lys Arg Gln  Asn Gln Leu His Pro
         1220                1225                1230

Ser Ser  Ala Gln Ser Arg  Ser Gly Gln Pro  Gln Lys Ala Ala Thr
         1235                1240                1245

Cys Lys  Val Ser Ser Ile  Asn Gln Glu Thr  Ile Gln Thr Tyr Cys
         1250                1255                1260

Val Glu  Asp Thr Pro Ile  Cys Phe Ser Arg  Cys Ser Ser Leu Ser
         1265                1270                1275

Ser Leu  Ser Ser Ala Glu  Asp Glu Ile Gly  Cys Asn Gln Thr Thr
         1280                1285                1290

Gln Glu  Ala Asp Ser Ala  Asn Thr Leu Gln  Ile Ala Glu Xaa Lys
         1295                1300                1305

Glu Lys  Ile Gly Thr Arg  Ser Ala Xaa Asp  Pro Val Ser Glu Val
         1310                1315                1320

Pro Ala  Val Ser Gln His  Pro Arg Thr Lys  Ser Ser Arg Leu Gln
         1325                1330                1335

Gly Ser  Ser Leu Ser Ser  Glu Ser Ala Arg  His Lys Ala Val Glu
         1340                1345                1350

Phe Ser  Ser Gly Ala Lys  Ser Pro Ser Lys  Ser Gly Ala Gln Thr
         1355                1360                1365

Pro Lys  Ser Pro Pro Glu  His Tyr Val Gln  Glu Thr Pro Leu Met
         1370                1375                1380

Phe Ser  Arg Cys Thr Ser  Val Ser Ser Leu  Asp Ser Phe Glu Ser
         1385                1390                1395

Arg Ser  Ile Ala Ser Ser  Val Gln Ser Glu  Pro Cys Ser Gly Met
         1400                1405                1410

Val Ser  Gly Ile Ile Ser  Pro Ser Asp Leu  Pro Asp Ser Pro Gly
         1415                1420                1425

Gln Thr  Met Pro Pro Ser  Arg Ser Lys Thr  Pro Pro Pro Pro
         1430                1435                1440

Gln Thr  Ala Gln Thr Lys  Arg Glu Val Pro  Lys Asn Lys Ala Pro
         1445                1450                1455

Thr Ala  Glu Lys Arg Glu  Ser Gly Pro Lys  Gln Ala Ala Val Asn
         1460                1465                1470

Ala Ala  Val Gln Arg Val  Gln Val Leu Pro  Asp Ala Asp Thr Leu
         1475                1480                1485

Leu His  Phe Ala Thr Glu  Ser Thr Pro Asp  Gly Phe Ser Cys Ser
         1490                1495                1500

Ser Ser  Leu Ser Ala Leu  Ser Leu Asp Glu  Pro Phe Ile Gln Lys
         1505                1510                1515

Asp Val  Glu Leu Arg Ile  Met Pro Pro Val  Gln Glu Asn Asp Asn
         1520                1525                1530

Gly Asn  Glu Thr Glu Ser  Glu Gln Pro Lys  Glu Ser Asn Glu Asn
         1535                1540                1545

Gln Glu  Lys Glu Ala Glu  Lys Thr Ile Asp  Ser Glu Lys Asp Leu
         1550                1555                1560

Leu Asp  Asp Ser Asp Asp  Asp Asp Ile Glu  Ile Leu Glu Glu Cys
         1565                1570                1575

Ile Ile  Ser Ala Met Pro  Thr Lys Ser Ser  Arg Lys Ala Lys Lys
         1580                1585                1590
```

```
Pro Ala Gln Thr Ala Ser Lys Leu Pro Pro Val Ala Arg Lys
    1595                1600                1605

Pro Ser Gln Leu Pro Val Tyr Lys Leu Leu Pro Ser Gln Asn Arg
    1610                1615                1620

Leu Gln Pro Gln Lys His Val Ser Phe Thr Pro Gly Asp Asp Met
    1625                1630                1635

Pro Arg Val Tyr Cys Val Glu Gly Thr Pro Ile Asn Phe Ser Thr
    1640                1645                1650

Ala Thr Ser Leu Ser Asp Leu Thr Ile Glu Ser Pro Pro Asn Glu
    1655                1660                1665

Leu Ala Ala Gly Glu Gly Val Arg Gly Gly Ala Gln Ser Gly Glu
    1670                1675                1680

Phe Glu Lys Arg Asp Thr Ile Pro Thr Glu Gly Arg Ser Thr Asp
    1685                1690                1695

Glu Ala Gln Gly Gly Lys Thr Ser Ser Val Thr Ile Pro Glu Leu
    1700                1705                1710

Asp Asp Asn Lys Ala Glu Glu Gly Asp Ile Leu Ala Glu Cys Ile
    1715                1720                1725

Asn Ser Ala Met Pro Lys Gly Lys Ser His Lys Pro Phe Arg Val
    1730                1735                1740

Lys Lys Ile Met Asp Gln Val Gln Gln Ala Ser Ala Ser Ser Ser
    1745                1750                1755

Ala Pro Asn Lys Asn Gln Leu Asp Gly Lys Lys Lys Lys Pro Thr
    1760                1765                1770

Ser Pro Val Lys Pro Ile Pro Gln Asn Thr Glu Tyr Arg Thr Arg
    1775                1780                1785

Val Arg Lys Asn Ala Asp Ser Lys Asn Asn Leu Asn Ala Glu Arg
    1790                1795                1800

Val Phe Ser Asp Asn Lys Asp Ser Lys Lys Gln Asn Leu Lys Asn
    1805                1810                1815

Asn Ser Lys Val Phe Asn Asp Lys Leu Pro Asn Asn Glu Asp Arg
    1820                1825                1830

Val Arg Gly Ser Phe Ala Phe Asp Ser Pro His His Tyr Thr Pro
    1835                1840                1845

Ile Glu Gly Thr Pro Tyr Cys Phe Ser Arg Asn Asp Ser Leu Ser
    1850                1855                1860

Ser Leu Asp Phe Asp Asp Asp Val Asp Leu Ser Arg Glu Lys
    1865                1870                1875

Ala Glu Leu Arg Lys Ala Lys Glu Asn Lys Glu Ser Glu Ala Lys
    1880                1885                1890

Val Thr Ser His Thr Glu Leu Thr Ser Asn Gln Gln Ser Ala Asn
    1895                1900                1905

Lys Thr Gln Ala Ile Ala Lys Gln Pro Ile Asn Arg Gly Gln Pro
    1910                1915                1920

Lys Pro Ile Leu Gln Lys Gln Ser Thr Phe Pro Gln Ser Ser Lys
    1925                1930                1935

Asp Ile Pro Asp Arg Gly Ala Ala Thr Asp Glu Lys Leu Gln Asn
    1940                1945                1950

Phe Ala Ile Glu Asn Thr Pro Val Cys Phe Ser His Asn Ser Ser
    1955                1960                1965

Leu Ser Ser Leu Ser Asp Ile Asp Gln Glu Asn Asn Asn Lys Glu
    1970                1975                1980
```

```
Asn Glu Pro Ile Lys Glu Thr Glu Pro Pro Asp Ser Gln Gly Glu
    1985                1990                1995

Pro Ser Lys Pro Gln Ala Ser Gly Tyr Ala Pro Lys Ser Phe His
    2000                2005                2010

Val Glu Asp Thr Pro Val Cys Phe Ser Arg Asn Ser Ser Leu Ser
    2015                2020                2025

Ser Leu Ser Ile Asp Ser Glu Asp Asp Leu Leu Gln Glu Cys Ile
    2030                2035                2040

Ser Ser Ala Met Pro Lys Lys Lys Lys Pro Ser Arg Leu Lys Gly
    2045                2050                2055

Asp Asn Glu Lys His Ser Pro Arg Asn Met Gly Gly Ile Leu Gly
    2060                2065                2070

Glu Asp Leu Thr Leu Asp Leu Lys Asp Ile Gln Arg Pro Asp Ser
    2075                2080                2085

Glu His Gly Leu Ser Pro Asp Ser Glu Asn Phe Asp Trp Lys Ala
    2090                2095                2100

Ile Gln Glu Gly Ala Asn Ser Ile Val Ser Ser Leu His Gln Ala
    2105                2110                2115

Ala Ala Ala Ala Cys Leu Ser Arg Gln Ala Ser Ser Asp Ser Asp
    2120                2125                2130

Ser Ile Leu Ser Leu Lys Ser Gly Ile Ser Leu Gly Ser Pro Phe
    2135                2140                2145

His Leu Thr Pro Asp Gln Glu Glu Lys Pro Phe Thr Ser Asn Lys
    2150                2155                2160

Gly Pro Arg Ile Leu Lys Pro Gly Glu Lys Ser Thr Leu Glu Thr
    2165                2170                2175

Lys Lys Ile Glu Ser Glu Ser Lys Gly Ile Lys Gly Gly Lys Lys
    2180                2185                2190

Val Tyr Lys Ser Leu Ile Thr Gly Lys Val Arg Ser Asn Ser Glu
    2195                2200                2205

Ile Ser Gly Gln Met Lys Gln Pro Leu Gln Ala Asn Met Pro Ser
    2210                2215                2220

Ile Ser Arg Gly Arg Thr Met Ile His Ile Pro Gly Val Arg Asn
    2225                2230                2235

Ser Ser Ser Ser Thr Ser Pro Val Ser Lys Lys Gly Pro Pro Leu
    2240                2245                2250

Lys Thr Pro Ala Ser Lys Ser Pro Ser Glu Gly Gln Thr Ala Thr
    2255                2260                2265

Thr Ser Pro Arg Gly Ala Lys Pro Ser Val Lys Ser Glu Leu Ser
    2270                2275                2280

Pro Val Ala Arg Gln Thr Ser Gln Ile Gly Gly Ser Ser Lys Ala
    2285                2290                2295

Pro Ser Arg Ser Gly Ser Arg Asp Ser Thr Pro Ser Arg Pro Ala
    2300                2305                2310

Gln Gln Pro Leu Ser Arg Pro Ile Gln Ser Pro Gly Arg Asn Ser
    2315                2320                2325

Ile Ser Pro Gly Arg Asn Gly Ile Ser Pro Pro Asn Lys Leu Ser
    2330                2335                2340

Gln Leu Pro Arg Thr Ser Ser Pro Ser Thr Ala Ser Thr Lys Ser
    2345                2350                2355

Ser Gly Ser Gly Lys Met Ser Tyr Thr Ser Pro Gly Arg Gln Met
    2360                2365                2370

Ser Gln Gln Asn Leu Thr Lys Gln Thr Gly Leu Ser Lys Asn Ala
```

```
                2375                2380                2385
Ser  Ser  Ile  Pro  Arg  Ser  Glu  Ser  Ala  Ser  Lys  Gly  Leu  Asn  Gln
     2390                2395                2400

Met  Asn  Asn  Gly  Asn  Gly  Ala  Asn  Lys  Lys  Val  Glu  Leu  Ser  Arg
     2405                2410                2415

Met  Ser  Ser  Thr  Lys  Ser  Ser  Gly  Ser  Glu  Ser  Asp  Arg  Ser  Glu
     2420                2425                2430

Arg  Pro  Val  Leu  Val  Arg  Gln  Ser  Thr  Phe  Ile  Lys  Glu  Ala  Pro
     2435                2440                2445

Ser  Pro  Thr  Leu  Arg  Arg  Lys  Leu  Glu  Glu  Ser  Ala  Ser  Phe  Glu
     2450                2455                2460

Ser  Leu  Ser  Pro  Ser  Ser  Arg  Pro  Ala  Ser  Pro  Thr  Arg  Ser  Gln
     2465                2470                2475

Ala  Gln  Thr  Pro  Val  Leu  Ser  Pro  Ser  Leu  Pro  Asp  Met  Ser  Leu
     2480                2485                2490

Ser  Thr  His  Ser  Ser  Val  Gln  Ala  Gly  Gly  Trp  Arg  Lys  Leu  Pro
     2495                2500                2505

Pro  Asn  Leu  Ser  Pro  Thr  Ile  Glu  Tyr  Asn  Asp  Gly  Arg  Pro  Ala
     2510                2515                2520

Lys  Arg  His  Asp  Ile  Ala  Arg  Ser  His  Ser  Glu  Ser  Pro  Ser  Arg
     2525                2530                2535

Leu  Pro  Ile  Asn  Arg  Ser  Gly  Thr  Trp  Lys  Arg  Glu  His  Ser  Lys
     2540                2545                2550

His  Ser  Ser  Ser  Leu  Pro  Arg  Val  Ser  Thr  Trp  Arg  Arg  Thr  Gly
     2555                2560                2565

Ser  Ser  Ser  Ser  Ile  Leu  Ser  Ala  Ser  Ser  Glu  Ser  Ser  Glu  Lys
     2570                2575                2580

Ala  Lys  Ser  Glu  Asp  Glu  Lys  His  Val  Asn  Ser  Ile  Ser  Gly  Thr
     2585                2590                2595

Lys  Gln  Ser  Lys  Glu  Asn  Gln  Val  Ser  Ala  Lys  Gly  Thr  Trp  Arg
     2600                2605                2610

Lys  Ile  Lys  Glu  Asn  Glu  Phe  Ser  Pro  Thr  Asn  Ser  Thr  Ser  Gln
     2615                2620                2625

Thr  Val  Ser  Ser  Gly  Ala  Thr  Asn  Gly  Ala  Glu  Ser  Lys  Thr  Leu
     2630                2635                2640

Ile  Tyr  Gln  Met  Ala  Pro  Ala  Val  Ser  Lys  Thr  Glu  Asp  Val  Trp
     2645                2650                2655

Val  Arg  Ile  Glu  Asp  Cys  Pro  Ile  Asn  Asn  Pro  Arg  Ser  Gly  Arg
     2660                2665                2670

Ser  Pro  Thr  Gly  Asn  Thr  Pro  Pro  Val  Ile  Asp  Ser  Val  Ser  Glu
     2675                2680                2685

Lys  Ala  Asn  Pro  Asn  Ile  Lys  Asp  Ser  Lys  Asp  Asn  Gln  Ala  Lys
     2690                2695                2700

Gln  Asn  Val  Gly  Asn  Gly  Ser  Val  Pro  Met  Arg  Thr  Val  Gly  Leu
     2705                2710                2715

Glu  Asn  Arg  Leu  Asn  Ser  Phe  Ile  Gln  Val  Asp  Ala  Pro  Asp  Gln
     2720                2725                2730

Lys  Gly  Thr  Glu  Ile  Lys  Pro  Gly  Gln  Asn  Asn  Pro  Val  Pro  Val
     2735                2740                2745

Ser  Glu  Thr  Asn  Glu  Ser  Ser  Ile  Val  Glu  Arg  Thr  Pro  Phe  Ser
     2750                2755                2760

Ser  Ser  Ser  Ser  Ser  Lys  His  Ser  Ser  Pro  Ser  Gly  Thr  Val  Ala
     2765                2770                2775
```

```
Ala Arg Val Thr Pro Phe Asn Tyr Asn Pro Ser Pro Arg Lys Ser
    2780            2785            2790

Ser Ala Asp Ser Thr Ser Ala Arg Pro Ser Gln Ile Pro Thr Pro
    2795            2800            2805

Val Asn Asn Asn Thr Lys Lys Arg Asp Ser Lys Thr Asp Ser Thr
    2810            2815            2820

Glu Ser Ser Gly Thr Gln Ser Pro Lys Arg His Ser Gly Ser Tyr
    2825            2830            2835

Leu Val Thr Ser Val
    2840

<210> SEQ ID NO 9
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 9
tttgcagggt attagcagaa tctgcttcct gtg                              33

<210> SEQ ID NO 10
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 10
ccaatctttt cttttttttc t                                           21

<210> SEQ ID NO 11
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 11
tgctgtgaca ctgctggaac ttcgc                                       25

<210> SEQ ID NO 12
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 12
cacaggatct tgagctgacc tag                                         23
```